(12) United States Patent
Lee

(10) Patent No.: US 10,631,823 B2
(45) Date of Patent: Apr. 28, 2020

(54) METHOD AND APPARATUS FOR DISPLAYING ULTRASONIC IMAGE

(71) Applicant: SAMSUNG MEDISON CO., LTD., Hongcheon-gun (KR)

(72) Inventor: Bong-heon Lee, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 922 days.

(21) Appl. No.: 15/103,555

(22) PCT Filed: Dec. 12, 2014

(86) PCT No.: PCT/KR2014/012272
§ 371 (c)(1),
(2) Date: Jun. 10, 2016

(87) PCT Pub. No.: WO2015/088277
PCT Pub. Date: Jun. 18, 2015

(65) Prior Publication Data
US 2016/0310101 A1 Oct. 27, 2016

(30) Foreign Application Priority Data
Dec. 12, 2013 (KR) .................. 10-2013-0154899

(51) Int. Cl.
*A61B 8/08* (2006.01)
*A61B 8/14* (2006.01)
*A61B 8/00* (2006.01)

(52) U.S. Cl.
CPC ............ *A61B 8/085* (2013.01); *A61B 8/0891* (2013.01); *A61B 8/14* (2013.01); *A61B 8/4427* (2013.01);
(Continued)

(58) Field of Classification Search
CPC ......... A61B 8/085; A61B 8/0891; A61B 8/14; A61B 8/4427; A61B 8/462; A61B 8/463;
(Continued)

(56) References Cited

U.S. PATENT DOCUMENTS 8,285,012 B2  10/2012 Kadomura et al.
8,447,082 B2  5/2013 Shirahata
(Continued)

FOREIGN PATENT DOCUMENTS

CN  101166470 A  4/2008
CN  101677798 A  3/2010
(Continued)

OTHER PUBLICATIONS

Communication dated Jul. 18, 2016 issued by the Korean Intellectual Property Office in counterpart Korean Patent Application No. 10-2014-0179360.
(Continued)

*Primary Examiner* — Michael T Rozanski
(74) *Attorney, Agent, or Firm* — Sughrue Mion, PLLC

(57) ABSTRACT

Disclosed is an ultrasound image display apparatus and method which provides a user with a 3D image enabling a tubular tissue to be easily diagnosed, thereby easily diagnosing whether a disease occurs in the tubular tissue. The ultrasound image display apparatus includes an image processor that generates a first image three-dimensionally representing a surface constituting a tubular tissue on a reference plane, based on ultrasound data corresponding to an object including the tubular tissue and a display that displays the first image.

18 Claims, 15 Drawing Sheets

(52) U.S. Cl.
CPC .............. *A61B 8/462* (2013.01); *A61B 8/463* (2013.01); *A61B 8/466* (2013.01); *A61B 8/5207* (2013.01); *A61B 8/5215* (2013.01); *A61B 8/5223* (2013.01); *A61B 8/467* (2013.01); *A61B 8/485* (2013.01); *A61B 8/523* (2013.01); *A61B 8/543* (2013.01)

(58) Field of Classification Search
CPC ......... A61B 8/466; A61B 8/467; A61B 8/485; A61B 8/5207; A61B 8/5215; A61B 8/5223; A61B 8/523; A61B 8/543
See application file for complete search history.

(56) References Cited

U.S. PATENT DOCUMENTS

| | | |
|---|---|---|
| 8,913,793 B2 | 12/2014 | Everett et al. |
| 9,449,387 B2 | 9/2016 | Wakai |
| 9,886,781 B2 | 2/2018 | Goto |
| 2004/0249270 A1 | 12/2004 | Kondo et al. |
| 2006/0279568 A1 | 12/2006 | Matsumoto |
| 2008/0051660 A1 | 2/2008 | Kakadaris et al. |
| 2009/0022387 A1 | 1/2009 | Shirahata et al. |
| 2010/0201683 A1 | 8/2010 | Shirahata et al. |
| 2010/0214283 A1 | 8/2010 | Lobregt et al. |
| 2011/0018871 A1 | 1/2011 | Shirahata |
| 2011/0255755 A1 | 10/2011 | Shirahata et al. |
| 2013/0315455 A1 | 11/2013 | Wakai |
| 2016/0071267 A1 | 3/2016 | Wakai |
| 2019/0240208 A1 | 8/2019 | Zarnitsyn et al. |

FOREIGN PATENT DOCUMENTS

| | | |
|---|---|---|
| CN | 103237901 A | 8/2013 |
| CN | 103402434 A | 11/2013 |
| CN | 104884049 A | 9/2015 |
| CN | 104968276 A | 10/2015 |
| JP | 2009-507537 A | 2/2009 |
| JP | 2009195585 A | 9/2009 |
| JP | 2011218082 A | 11/2011 |
| JP | 2012196437 A | 10/2012 |
| JP | 201352131 A | 3/2013 |
| JP | 2013118932 A | 6/2013 |

OTHER PUBLICATIONS

Communication dated Oct. 11, 2017, from the European Patent Office in counterpart European Application No. 14869861.6.
Communication dated Feb. 27, 2015, issued by the International Searching Authority in counterpart International Application No. PCT/KR2014/012272 (PCT/ISA/210 & PCT/ISA/237).
Communication dated Apr. 21, 2016, issued by the Korean Intellectual Property Office in counterpart Korean Application No. 10-2014-0179360.
Communication dated Aug. 29, 2018, from the State Intellectual Property Office of People's Republic of China in counterpart Application No. 201480075482.5.
Communication dated Apr. 9, 2019 issued by the State Intellectual Property Office of P.R. China in counterpart Chinese Application No. 201480075482.5.
Communication dated Aug. 26, 2019 by the State Intellectual Property Office of P.R. China in counterpart Chinese Patent Application No. 201480075482.5.
Communication dated Mar. 6, 2020, issued by the European Patent Office in counterpart European Patent Application No. 14 869 861.6.
Communication dated Jan. 3, 2020, issued by the Chinese Patent Office in counterpart Chinese Patent Application No. 201480075482.5.

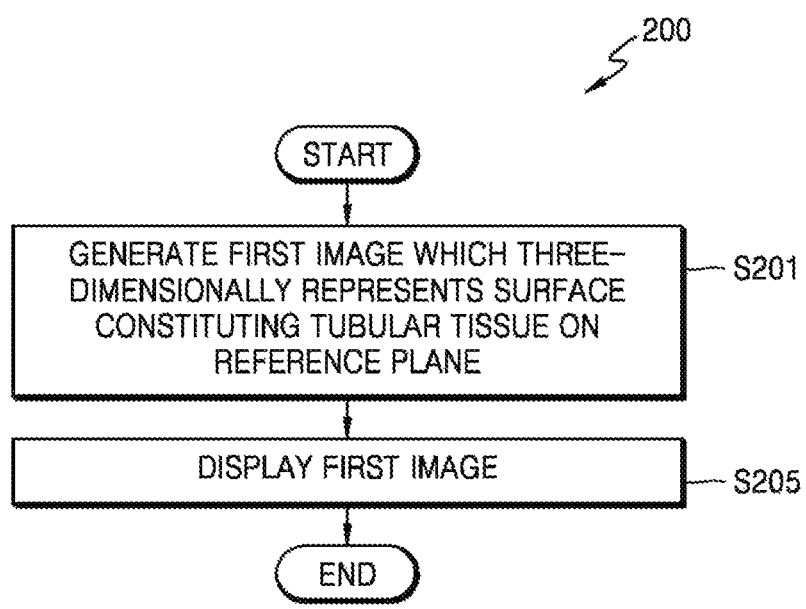

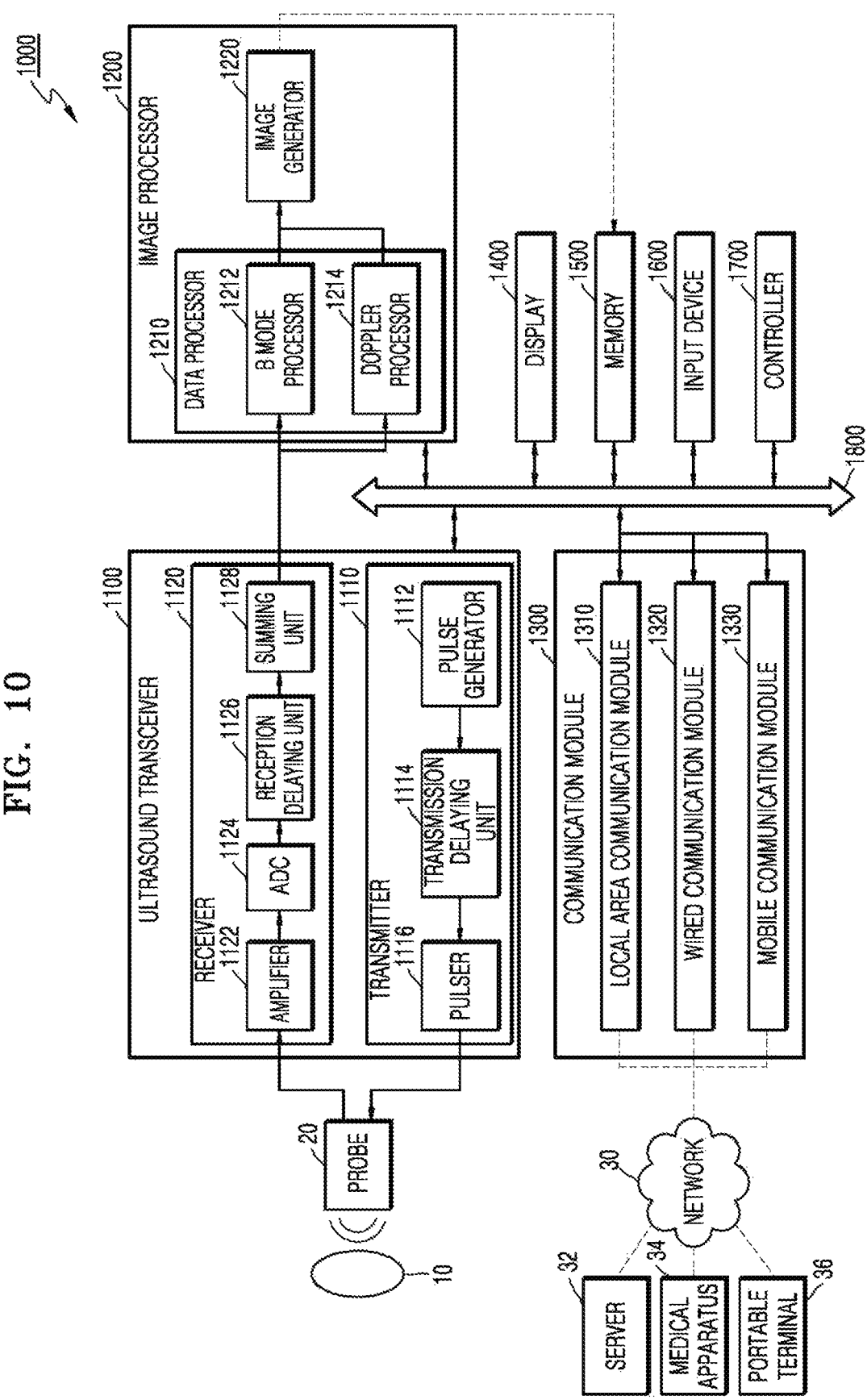

METHOD AND APPARATUS FOR DISPLAYING ULTRASONIC IMAGE

TECHNICAL FIELD

One or more exemplary embodiments relate to a method and apparatus for displaying an ultrasound image, and more particularly, to a method and apparatus for displaying an ultrasound image, which provide a three-dimensional (3D) ultrasound image of a tubular tissue.

BACKGROUND ART

As an ultrasound system has noninvasive and nondestructive characteristics, it is widely used in medical applications for obtaining information about the internal structure of an object. The ultrasound system provides in real time a high-resolution image of an internal tissue of an object to a medical practitioner, without requiring a surgical operation to directly make an incision in the body to observe the object.

Generally, in a state where a probe contacts a surface of an object, the ultrasound system transmits an ultrasound signal to the object and receives an ultrasound signal (hereinafter referred to as an echo signal) reflected from the object. The ultrasound system generates an ultrasound image of the object, based on the echo signal received through the probe and displays the generated ultrasound image in a display. The ultrasound image is expressed as a brightness (B) mode image using a reflection coefficient based on an acoustic impedance difference between tissues.

A carotid artery among a plurality of blood vessels included in the human body is a blood vessel that connects a main artery to a brain blood vessel, and there are two carotid arteries which are respectively disposed on the left and the right of the neck. About 80% of blood flowing to the brain passes through the carotid artery. A carotid artery examination using the ultrasound system is a useful examination method that accurately evaluates a degree of stenosis of the carotid artery.

Generally, an image of one slice of a blood vessel is used for diagnosing a degree of stenosis of the blood vessel. However, it is difficult to know an overall degree of stenosis of a blood vessel by using only an image of one slice of the blood vessel.

DETAILED DESCRIPTION OF THE INVENTION

Technical Problem

One or more exemplary embodiments may provide an ultrasound image enabling an object having a tubular tissue to be easily diagnosed.

One or more exemplary embodiments may provide a 3D image of a blood vessel for accurately and conveniently diagnosing a degree of stenosis of a blood vessel.

Advantageous Effects of the Invention

According to the one or more exemplary embodiments, the ultrasound image display apparatus and method generate and display an ultrasound image which three-dimensionally represents an unfolded tubular tissue on a reference plane, thereby enabling a user to easily diagnose the inside and the outside of the tubular tissue.

Accordingly, an accuracy of a disease diagnosis increases.

BRIEF DESCRIPTION OF THE DRAWINGS

FIG. 2A is a flowchart of an ultrasound image display method according to exemplary embodiments;

FIG. 10 is a block diagram of an ultrasound system to which an ultrasound image display apparatus is applied, according to exemplary embodiments.

BEST MODE

Figure 1A:
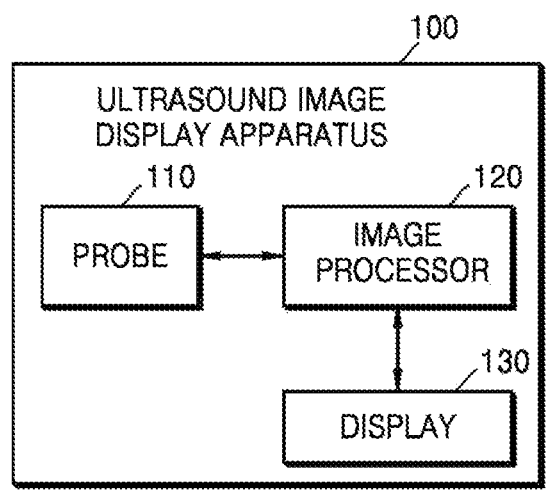
FIGS. 1A and 1B are a block diagrams of an ultrasound image display apparatus according to exemplary embodiments.

According to one or more exemplary embodiments, an ultrasound image display apparatus includes: an image processor that generates a first image three-dimensionally representing a surface constituting a tubular tissue on a reference plane, based on ultrasound data corresponding to an object including the tubular tissue; and a display that displays the first image.

The first image may be a three-dimensional (3D) image that represents an unfolded surface constituting the tubular tissue.

The image processor may sense at least one selected from a certain part and a certain tissue which are located on the surface constituting the tubular tissue, based on the ultrasound data and marks at least one, selected from the sensed certain part and the sensed certain tissue, on the surface constituting the tubular tissue to generate the first image.

The image processor may acquire first region data that includes at least one selected from at least two two-dimensional (2D) ultrasound images enabling a three-dimensional shape of the tubular tissue to be acquired and three-dimensional (3D) data three-dimensionally expressing the tubular tissue, based on the ultrasound data and generates the first image, based on the first region data.

The image processor may detect a first region corresponding to the tubular tissue from first volume data which is acquired based on the ultrasound data, map volume data corresponding to the first region to the reference plane to generate second volume data, and generate the first image, based on the second volume data.

The image processor may acquire a plurality of two-dimensional (2D) ultrasound images corresponding to a plurality of continuous slices, based on the ultrasound data, acquire a three-dimensional shape of the tubular tissue, based on the plurality of 2D ultrasound images, and generate the first image, based on the three-dimensional shape of the tubular tissue.

The tubular tissue may include a blood vessel, the first region may include a blood vessel region, and the image processor may generate the first image representing information about plaque included in the blood vessel.

The image processor may detect a first region corresponding to the tubular tissue from first volume data which is acquired based on the ultrasound data, set a cut line for the first region in a lengthwise direction of the tubular tissue, and cut the first region along the cut line to generate the first image that represents an unfolded surface constituting the tubular tissue.

The display may further display a second image that is a three-dimensional (3D) ultrasound image that is generated based on first volume data which is acquired based on the ultrasound data and represents the tubular tissue.

The ultrasound image display apparatus may further include a user interface that receives a first user input for setting a cut line, which is parallel to a lengthwise direction of the tubular tissue, in the second image, wherein the image processor may set a cut line for the first region corresponding to the tubular tissue included in the first volume data, based on the first user input and cut the first region along the cut line to generate the first image that represents an unfolded surface constituting the tubular tissue.

The image processor may detect a plaque region corresponding to the plaque, based on the ultrasound data, generate a plaque image representing the plaque region, and generate the first image including the plaque image.

The image processor may generate the plaque image in which a contour is marked, based on a height of the plaque region.

The image processor may generate the plaque image to which at least one color determined based on the height of the plaque region is mapped.

The image processor may map at least one color to the plaque region to generate the plaque image, based on at least one selected from a ratio of a height of the plaque region and a diameter of the blood vessel, an elasticity value of the plaque region, and a brightness value of an image in the plaque region.

The image processor may generate the plaque image so that plaque which protrudes inward into the tubular tissue with reference to the reference plane and plaque which protrudes outward from the tubular tissue with reference to the reference plane are differentially marked.

The image processor may detect a plurality of plaque regions corresponding to the plaque, based on the ultrasound data, generate a plaque image representing the plurality of plaque regions, and generate the first image including the plaque image, and the plaque image may include a plurality of identifiers respectively corresponding to the plurality of plaque regions.

The ultrasound image display apparatus may further include a user interface that receives a second user input for rotating the first image, wherein the image processor may perform control to display a rotated image which is obtained by rotating the first image, based on the second user input.

The ultrasound image display apparatus may further include a probe that transmits an ultrasound signal to the object and receives an echo signal reflected from the object, wherein the image processor may receive the ultrasound data including the echo signal.

According to one or more exemplary embodiments, an ultrasound image display method includes: generating a first image three-dimensionally representing a surface constituting a tubular tissue on a reference plane, based on ultrasound data corresponding to an object including the tubular tissue; and displaying the first image.

Mode of the Invention

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. In the accompanying drawings, a portion irrelevant to a description of the inventive concept will be omitted for clarity. Moreover, like reference numerals refer to like elements throughout.

In this disclosure below, when one part (or element, device, etc.) is referred to as being 'connected' to another part (or element, device, etc.), it should be understood that the former may be 'directly connected' to the latter, or 'electrically connected' to the latter via an intervening part (or element, device, etc.). When a part "includes" or "comprises" an element, unless there is a particular description contrary thereto, the part can further include other elements, not excluding the other elements.

Throughout the specification, an "ultrasound image" refers to an image of an object, which is obtained using ultrasound waves. The term "object" used herein may be an animate thing or an inanimate thing, which is to be expressed as an image. Also, an object may mean a part of a human body, and may include an organ such as a liver, a heart, a womb, a brain, breasts, an abdomen, or the like, or a fetus. Moreover, the term "user" used herein is a medical expert, and may be a doctor, a nurse, a medical technologist, a sonographer, a medical image expert, or the like. However, the user is not limited thereto.

Hereinafter, exemplary embodiments will be described in detail with reference to the accompanying drawings.

FIG. 1 is a block diagram of an ultrasound image display apparatus 100 according to exemplary embodiments.

As illustrated in FIG. 1A, the ultrasound image display apparatus 100 according to exemplary embodiments includes an image processor 120 and a display 130. Also, the ultrasound image display apparatus 100 may further include a probe 110.

The ultrasound image display apparatus 100 may be an arbitrary image display apparatus that processes and displays an ultrasound image.

In detail, the ultrasound apparatus 1000 may be implemented in a portable type as well as a cart type. Examples of portable ultrasound diagnosis apparatuses may include, but are not limited to, a picture archiving and communication system (PACS) viewer, a smartphone, a laptop computer, a personal digital assistant (PDA), and a tablet PC.

Moreover, the ultrasound image display apparatus 100 may include the probe 110. When the ultrasound image display apparatus 100 includes the probe 110, the ultrasound image display apparatus 100 may generate a first image for a diagnosis, based on ultrasound data (for example, an ultrasound echo signal) received from the probe 110. Also, the probe 110 may be a wired probe or a wireless probe.

Moreover, the ultrasound image display apparatus 100 may not include the probe 110, and the probe 110 may externally receive ultrasound data including an ultrasound echo signal which is obtained by ultrasound-scanning an object. In this case, the image processor 120 may receive the ultrasound data from an external server (not shown), an ultrasound diagnosis apparatus (not shown), or a medical imaging system (not shown). In detail, the image processor 120 may include a communication module (not shown) that transmits or receives data to or from the external server (not shown), the ultrasound diagnosis apparatus (not shown), or the medical imaging system (not shown) over a wired/wireless communication network. The image processor 120 may receive the ultrasound data through the communication module (not shown). In detail, the probe 110 may transmit an ultrasound signal to the object and receive an echo signal reflected from the object. The probe 110 may transmit the ultrasound signal to the object according to a driving signal applied to the probe 110 and receive the echo signal reflected from the object.

The probe 110 includes a plurality of transducers, and the plurality of transducers oscillate in response to electric signals and generate acoustic energy, that is, ultrasound waves. Also, the probe 110 may be connected to a body of the ultrasound image display apparatus 100 by wire or wirelessly, and the ultrasound image display apparatus 100 may include a plurality of probes 110 depending on an implementation type. The probe 110 according to exemplary embodiments may include at least one selected from a one-dimensional (1D) probe, a 1.5-dimensional (1.5D) probe, a two-dimensional (2D) probe, and a 3D probe.

The image processor 120 generates a first image that three-dimensionally represents a surface constituting a tubular tissue on a reference plane, based on ultrasound data corresponding to an object including the tubular tissue. The object is a diagnosis target and includes a body part of a patient. In detail, the object may include the tubular tissue. At least one selected from the inside and the outside of the tubular tissue is observed in detail for diagnosing a disease. In exemplary embodiments, the first image for easily observing at least one selected from the inside and the outside of the tubular tissue is provided.

Here, the tubular tissue may be at least one selected from all body tissues and organs which have a tube shape. In detail, the tubular tissue may be a digestive organ such as a small intestine, a large intestine, a stomach, an esophagus, or a duodenum. Also, the tubular tissue may be a blood vessel. Also, the tubular tissue may be a urethral canal or a prostate.

The first image may be a 3D image that represents an unfolded tubular tissue. Also, the reference plane denotes a plane for showing an unfolded tubular tissue. In detail, the reference plane may be an outer boundary surface of the tubular tissue or an inner boundary surface of the tubular tissue. Also, the reference plane may be a 2D plane for showing an unfolded tubular tissue. The first image denotes an image where a surface of the tubular tissue is three-dimensionally marked by marking, on the reference plane, at least one selected from an inner surface and an outer surface which constitute the tubular tissue.

Moreover, the ultrasound data denotes data which is acquired by ultrasound-scanning the object. The ultrasound data may include the ultrasound echo signal received through the probe 110. Also, the ultrasound data may be 2D ultrasound data or volume data, based on the ultrasound echo signal.

In detail, the image processor 120 may acquire first region data which includes at least one selected from at least two 2D ultrasound images which enable a three-dimensional shape of the tubular tissue to be acquired and 3D data which three-dimensionally expresses the tubular tissue, based on the ultrasound data. The image processor 120 may generate the first image, based on the first region data.

In detail, the image processor 120 may acquire a plurality of 2D ultrasound images respectively corresponding to a plurality of slices which are continued, based on the ultrasound data and acquire a three-dimensional shape of the tubular tissue, based on the plurality of 2D ultrasound images. The image processor 120 may extract a boundary of the object included in each of the plurality of 2D ultrasound images respectively corresponding to the continued plurality of slices, and acquire the three-dimensional shape of the object including the tubular tissue by connecting the boundaries of the object included in the respective 2D ultrasound images. Therefore, the image processor 120 may acquire the three-dimensional shape of the tubular tissue by using the plurality of 2D ultrasound images which are acquired based on the ultrasound data.

Moreover, the image processor 120 may detect a first region corresponding to the tubular tissue from first volume data which is acquired based on the ultrasound data, and generate second volume data by mapping volume data, corresponding to the first region, to the reference plane. The image processor 120 may generate the first image, based on the second volume data.

In detail, the image processor 120 may acquire the first volume data, based on the ultrasound data corresponding to the object. Here, the ultrasound data may include the ultrasound echo signal received by the probe 110. Alternatively, the ultrasound data may be data which is acquired by processing the ultrasound echo signal. The first volume data denotes data where the object is expressed to have certain volume, based on the ultrasound data corresponding to the object.

In detail, the image processor 120 may process the echo signal received by the probe 110 to generate the ultrasound data. The image processor 120 may generate an ultrasound image by performing a scan conversion operation on the generated ultrasound data.

The ultrasound image may be a Doppler image representing a motion of an object, in addition to a grayscale ultrasound image which is generated by scanning the object according to an amplitude (A) mode, a brightness (B) mode, or a motion (M) mode. The Doppler image may be a blood flow Doppler image showing flow of blood (also referred to as a color Doppler image), a tissue Doppler image showing a movement of tissue, or a spectral Doppler image showing a moving speed of an object as a waveform.

Moreover, the image processor 120 may process the ultrasound data to generate volume data, and perform a volume rendering operation on the volume data to generate a 3D ultrasound image. Also, the image processor 120 may further generate an elastic image which is obtained by imaging a degree of deformation of the object based on a pressure, and may mark various additional information on the ultrasound image in texts or graphics.

In detail, the image processor 120 acquires the first volume data, based on the ultrasound data corresponding to the object. The image processor 120 detects the first region, corresponding to the tubular tissue included in the object, from the first volume data and generates the second volume data by mapping the volume data, included in the first region, to the reference plane. The image processor 120 generates the first region representing a surface constituting the tubular tissue by using the second volume data.

For example, the first image may be an image representing an inner surface of the tubular tissue. In detail, the first image may be an image representing an unfolded inner surface of the tubular tissue. Also, the first image may be a virtual endoscope image having the same view as that of an image which is acquired through endoscopy for the inside of the tubular tissue. In detail, the virtual endoscope image may be displayed by using a method such as fish's eye and perspective. The virtual endoscope image enables a user to intuitively recognize the inner surface of the tubular tissue having a tubular shape.

Moreover, the first image may be an image which represents at least one selected from the inner surface and the outer surface constituting the tubular tissue. In detail, the first image may be an image which represents an unfolded inner surface and an unfolded outer surface constituting the tubular tissue. Also, the first image may be an image which represents a thickness difference between the inner surface and the outer surface constituting the tubular tissue. Also, the first image may be an image which differentially represents the inner surface and the outer surface constituting the tubular tissue.

For example, in Crohn's disease, the inside of a colon may be diagnosed. In Crohn's disease, according to seriousness of disease, a shape of a wall of a colon may be changed, or a perforation may be formed because the wall swells or bursts. In this case, whether the wall swells or the perforation occurs may be diagnosed by observing an inner wall and/or an outer wall of the colon. In this case, the first image may be an image which represents an unfolded inner wall, which is an inner surface of the colon, and/or an unfolded outer wall which is an outer surface of the colon. A user easily diagnoses whether the inner wall or the outer wall of the colon swells or a perforation occurs, by using the first image.

As another example, when a disease occurs due to blood vessel stenosis, whether stenosis occurs in a blood vessel may be diagnosed for prevention or treatment. For example, as a representative example of a case where it is required to diagnose blood vessel stenosis, there is coronary artery stenosis. The coronary artery stenosis causes severe diseases such as myocardial infarction, arrhythmia, and angina, and thus, a stenosed blood vessel may be expanded or removed through an accurate diagnosis. To this end, by using a medical image, a stenosed blood vessel may be found, and a degree of stenosis of the stenosed blood vessel may be accurately observed and diagnosed.

Therefore, the tubular tissue may include a blood vessel that is a diagnosis target, the first region may include a blood vessel region, and the first image may be an image which represents a surface constituting the blood vessel.

The image processor 120 may detect the first region corresponding to the tubular tissue from the first volume data which is acquired based on the ultrasound data, and set a cut line for the first region in a lengthwise direction of the tubular tissue. Also, the image processor 120 may cut the first region along the cut line to generate the first image which represents an unfolded surface constituting the tubular tissue. The first image will be described in detail with reference to FIGS. 3A and 4A.

Hereinafter, a case where the tubular tissue includes a blood vessel and the first region is a blood vessel region will be described and be illustrated as an example.

In detail, the image processor 120 detects the first region, corresponding to the tubular tissue included in the object, from the first volume data. In detail, the image processor 120 detects a blood vessel region, corresponding to a blood vessel included in the object, from the first volume data. In the present embodiment, examples of a blood vessel used to diagnose a degree of stenosis of a blood vessel may include a carotid artery, a varicose vein, a coronary artery, etc. Also, a stenosis of a blood vessel is caused by plaque which exists in the blood vessel, and thus, the image processor 120 may generate the first image representing information about the plaque included in the blood vessel that is the tubular tissue.

In detail, when the reference plane is set as an inner wall of a blood vessel, the image processor 120 maps volume data, included in the blood vessel region, to a plane corresponding to the inner wall of the blood vessel to generate the second volume data. Also, the image processor 120 may set the reference plane as a plane which is generated by unfolding a plane which is set between the inner wall and an outer wall of the blood vessel. The image processor 120 may generate the first image representing a surface constituting the blood vessel, based on the second volume data.

In detail, the image processor 120 may set a cut line parallel to a lengthwise direction of the blood vessel, for the blood vessel region included in the first volume data. The image processor 120 may generate the second volume data in order for both ends of the plane, corresponding to the inner wall of the blood vessel included in the second volume data, to correspond to the cut line which is set for the blood vessel region. The second volume data may be volume data that shows an unfolded inner wall of the blood vessel. The image processor 120 may generate the first region which is a 3D image representing the inner wall constituting the blood vessel, based on the second volume data which shows an unfolded inner wall of the blood vessel.

Moreover, the image processor 120 may sense at least one selected from a certain part and a certain tissue which are located on a surface constituting the tubular tissue, based on the second volume data and mark at least one selected from the sensed part and tissue on the surface constituting the tubular tissue to generate the first region.

In detail, the image processor 120 may sense a certain tissue which is located on the inner wall constituting the blood vessel, based on the second volume data. In detail, the image processor 120 may sense a certain tissue such as plaque which causes a disease, and generate the first image which represents information about at least one selected from the presence, a position, a size, and a shape of the certain tissue. Here, the certain tissue may be a certain tissue, a body part, an abnormal part, or a disease-suspected part which are included in the tubular tissue. For example, the certain tissue may be a perforation of a colon, plaque of a blood vessel, a malignant tumor of a stomach, or an abnormal tissue which occurs in the stomach.

Moreover, the image processor 120 may sense a body part or a tissue which needs observation for diagnosing a disease in the tubular tissue, and generate the first image which represents the sensed body part or tissue. In the above-described exemplary embodiment, when the perforation exists in the colon, the image processor 120 may generate the first image where the perforation is marked. Also, when a tumor tissue exists in an inner wall of a stomach, the image processor 120 may mark the tumor tissue on the first image representing the inner wall of the stomach.

In detail, when the tubular tissue is a blood vessel, the image processor 120 may generate the first image which represents information about plaque included in the blood vessel. The plaque is a deposit which is deposited on an inner wall of the blood vessel and causes a stenosis of the blood vessel, and denotes an atherosclerotic plaque. Examples of the plaque may include a fiber plaque and a lipid plaque.

The image processor 120 may set a cut line parallel to a lengthwise direction of the blood vessel, for the blood vessel region included in the first volume data. The image processor 120 may generate the second volume data in order for both ends of the plane, corresponding to the inner wall of the blood vessel included in the second volume data, to correspond to the cut line which is set for the blood vessel region.

The image processor 120 may detect a plaque region, corresponding to the plaque, from the second volume data. The image processor 120 may generate a plaque image representing the plaque region and generate the first image including the plaque image.

In this case, the plaque image generated by the image processor 120 may be an image, where a contour is marked based on a height of the detected plaque region, or an image to which at least one or more colors determined based on the height of the detected plaque region is mapped. Also, the image processor 120 may detect a plurality of plaque regions, corresponding to the plaque, from the second volume data. The image processor 120 may generate a plaque image representing the plurality of plaque regions and generate the first image including the plaque image. At this time, the image processor 120 may generate the plaque image which includes a plurality of identifiers respectively corresponding to the plurality of plaque regions.

The display 130 may display the ultrasound image generated by the image processor 120. The display 130 may display various information, processed by the ultrasound image display apparatus 100, as well as the ultrasound image on a screen through a graphic user interface (GUI). The ultrasound image display apparatus 100 may include two or more the displays 130 depending on an implementation type. The display 130 according to exemplary embodiments may display the first image generated by the image processor 120.

Figure 1B:
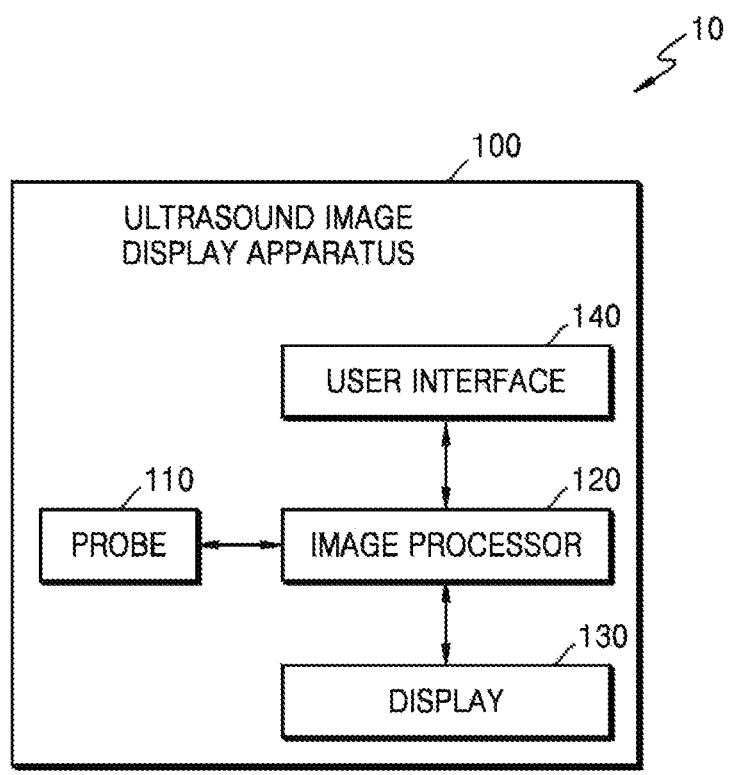

As illustrated in FIG. 1B, an ultrasound image display apparatus 100 according to exemplary embodiments may further include a user interface 140 unlike the ultrasound image display apparatus 100 of FIG. 1A. Therefore, in describing the ultrasound image display apparatus 100 of FIG. 1B, the same descriptions provided with regard to the ultrasound image display apparatus 100 of FIG. 1A are not repeated.

The user interface 140 may receive a user input. The user interface 140 may denote a means for inputting data used for a user to control the ultrasound image display apparatus 100. For example, the user interface 140 may include a keypad, a dome switch, a touch pad (for example, a contact capacitive type, a press resistive type, an infrared sensing type, a surface ultrasound conductive type, an integration tension measurement type, and a piezo effect type), a jog wheel, and a jog switch, but is not limited thereto. Also, a touch pad which forms a layer structure with a display panel of the display unit 130 may be referred to as a touch screen.

The display 130 may further display the second image which is generated based on the first volume data, and the user interface 140 may receive a user input for the second image displayed by the display 130. The image processor 120 may set a cut line for the first region corresponding to the tubular tissue included in the first volume data, based on the user input.

Moreover, the display 130 may display an image which is obtained by moving the first image, based on a user input received through the user input 140. In detail, the display 130 may provide a GUI for setting a cut line and a GUI through which a direction and an angle for rotating the first image are input. The user interface 140 may receive, from a user, a user input for rotating the first image. Then, the image processor 120 may perform control in order for the first image to be rotated at a certain angle in a certain direction and displayed, based on the user input.

The ultrasound image display apparatus 100 according to exemplary embodiments may mark plaque, which is located on an inner wall of a cylindrical blood vessel, on a plane and thus enables the user to quickly and accurately recognize a size, a shape, and a position distribution of the plaque and to quickly and accurately diagnose a degree of stenosis of a blood vessel. Hereinafter, a method in which the ultrasound image display apparatus 100 according to exemplary embodiments displays an ultrasound image of a blood vessel will be described in detail with reference to FIG. 2A.

FIG. 2A is a flowchart of an ultrasound image display method 200 according to exemplary embodiments. The ultrasound image display method 200 according to exemplary embodiments illustrated in FIG. 2A includes an operation and a configuration feature of the ultrasound image display apparatus 100 described above with reference to FIGS. 1A and 1B. Therefore, in describing the ultrasound image display method 200 according to exemplary embodiments illustrated in FIG. 2A, the same descriptions provided with regard to FIGS. 1A and 1B are not repeated.

Referring to FIG. 2A, in operation S201, the ultrasound image display method 200 may generate a first image which three-dimensionally represents a surface constituting a tubular tissue on a reference plane, based on ultrasound data corresponding to an object including the tubular tissue. Operation S201 may be performed by the image processor 120.

In operation S205, the ultrasound image display method 200 may display the generated first image. Operation S205 may be performed by the display 130.

Figure 2B:
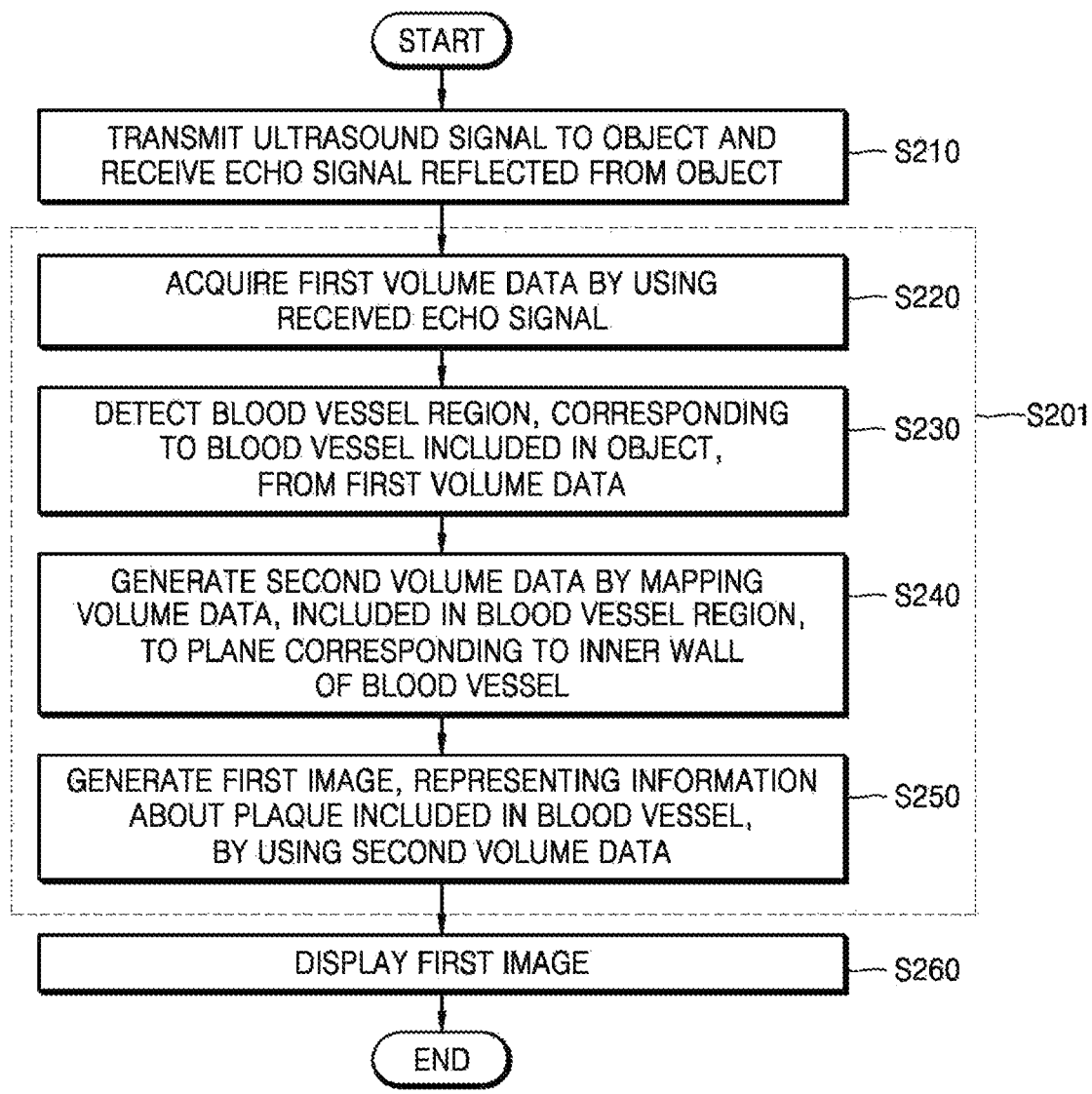
FIG. 2B is a flowchart of an ultrasound image display method according to exemplary embodiments.

FIG. 2B is a flowchart of an ultrasound image display method according to exemplary embodiments. The ultrasound image display method according to exemplary embodiments illustrated in FIG. 2B includes an operation and a configuration feature of the ultrasound image display apparatus 100 described above with reference to FIGS. 1A and 1B. Operations S220, S230, S240, and S250 illustrated in FIG. 2B correspond to operation S201 of FIG. 2A, and operation S260 of FIG. 2B corresponds to operation S205 of FIG. 2A. Therefore, in describing the ultrasound image display method according to exemplary embodiments illustrated in FIG. 2B, the same descriptions provided with regard to FIGS. 1A, 1B, and 2A are not repeated.

In operation S210, the ultrasound image display apparatus 100 according to exemplary embodiments may transmit an ultrasound signal to an object, and receive an echo signal reflected from the object.

In operation S220, the ultrasound image display apparatus 100 according to exemplary embodiments may acquire first volume data by using the received echo signal. The ultrasound image display apparatus 100 may acquire ultrasound image data about a plurality of slices included in the object. The ultrasound image display apparatus 100 may reconstruct the ultrasound image data about the plurality of slices to generate the first volume data about the object.

The ultrasound image display apparatus 100 may acquire the first volume data in consideration of electrocardiography (ECG). The ultrasound image display apparatus 100 may consider ECG for acquiring the first volume data which enables a stenosis of a blood vessel to be accurately diagnosed. The ultrasound image display apparatus 100 may consider ECG for determining a timing when the first volume data is acquired. For example, the ultrasound image display apparatus 100 may acquire the first volume data at a telophase of a heart systole or a telophase of a heart diastole.

In operation S230, the ultrasound image display apparatus 100 according to exemplary embodiments may detect a blood vessel region, corresponding to a blood vessel included in the object, from the first volume data. The ultrasound image display apparatus 100 may perform a noise filtering operation on the first volume data before detecting the blood vessel region, for increasing an accuracy of detection of the blood vessel region.

A method of acquiring second volume data and generating a first image will be described in detail with reference to FIG. 3A.

Figure 3A:
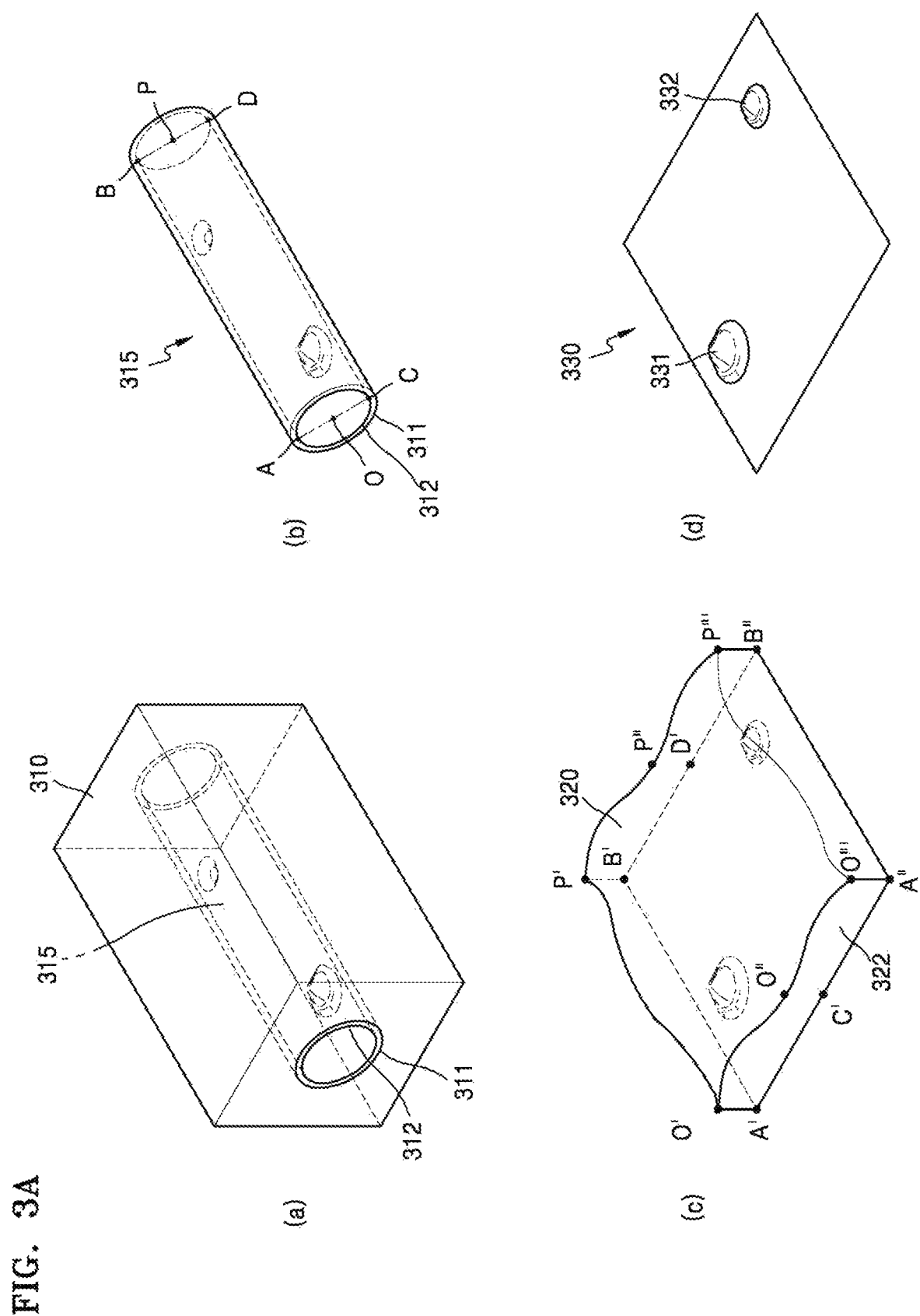
FIG. 3A is a conceptual diagram for describing a method of generating a first image according to exemplary embodiments.

FIG. 3A is a conceptual diagram for describing a method of generating a first image according to exemplary embodiments. In FIG. 3A, a case where a tubular tissue is a blood vessel is illustrated as an example. Also, a case where the image processor 120 senses plaque which exists in a tubular tissue and generates a first image where the plaque is marked is illustrated as an example.

FIG. 3A (a) illustrates first volume data 310 which is generated based on ultrasound data acquired from an object. The first volume data 310 is volume data representing the object, and includes a tubular tissue having a cylindrical shape.

In detail, FIG. 3A (a) illustrates an example of the first volume data 310 acquired from the object including a blood vessel. The ultrasound image display apparatus 100 may detect a first region, corresponding to the tubular tissue, from the first volume data 310. In detail, the ultrasound image display apparatus 100 may analyze the first volume data 310 to detect a blood vessel region 315 corresponding to the blood vessel. The blood vessel region 315 may be generated by an outer wall region 311, which is an outer surface of the blood vessel, and an inner wall region 312.

The ultrasound image display apparatus 100 may estimate a blood vessel wall by calculating a brightness or a gradient of each of pixels constituting the first volume data 310 or an ultrasound signal received from a probe, and detect a blood vessel region, based on the estimated blood vessel wall. For example, the ultrasound image display apparatus 100 according to exemplary embodiments may detect the blood vessel region by using an intima-media thickness (IMT) measurement method known to one of ordinary skill in the art.

The ultrasound image display apparatus 100 may detect an inflection point of a graph showing a brightness of a pixel to detect the blood vessel region 315 by using characteristic where a blood vessel is darkly shown in the first volume data 310 and the inner wall region 312 and the outer wall region 311 of the blood vessel which correspond to a boundary of the blood vessel are brightly shown.

In operation S240, the ultrasound image display apparatus 100 according to exemplary embodiments may generate the second volume data by mapping volume data, included in the first region, to a reference plane. In detail, the ultrasound image display apparatus 100 may generate the second volume data by mapping volume data, included in a blood vessel region, to a plane corresponding to an inner wall of a blood vessel.

The ultrasound image display apparatus 100 may generate second volume data 320 having a shape which is flatly unfolded by cutting a tubular tissue, in order for a user to easily recognize at least one selected from an inner wall and an outer wall of the tubular tissue or a certain tissue or a certain part (for example, plaque, a perforation, or a swelled part) which is located on at least one selected from the inner wall and the outer wall of the tubular tissue.

In detail, as illustrated in FIG. 3A (a), plaque may be located on a lower side surface or an upper side surface of an inner wall of a blood vessel having a cylindrical shape in obtaining information about the plaque, which is located inside the blood vessel, by using the first volume data 315. Therefore, it is difficult to quickly recognize a shape, a size, a height, and a position distribution of plaque, which is located on a top or a side surface of the inner wall of the blood vessel, by using only a 3D image which is generated by rendering the first volume data 315.

Therefore, as illustrated in FIGS. 3A (b) and (c), the ultrasound image display apparatus 100 according to exemplary embodiments may generate a first image 320 which three-dimensionally represents a surface constituting a tubular tissue on a reference plane. Also, in FIG. 3A (c), in the first image 320 where the tubular tissue is unfolded, a case where a surface constituting the tubular tissue and a part constituting the tubular tissue are expressed to have volume sensitivity is illustrated as an example.

In detail, the image processor 120 may generate the second volume data 320 having a shape, which is flatly unfolded by cutting a cylindrical blood vessel region in a lengthwise direction, by using the first volume data 315. A 3D image corresponding to the second volume data 320 may be generated as a first image.

In detail, the ultrasound image display apparatus 100 may set a cut line for the detected blood vessel region and rearrange the first volume data 315 on a plane with respect to the cut line to generate the second volume data 320.

For example, the ultrasound image display apparatus 100 may set a cut line parallel to a lengthwise direction of the blood vessel region. Also, the ultrasound image display apparatus 100 may set a cut line parallel to a direction in which blood flows in the blood vessel region. As another example, the ultrasound image display apparatus 100 may display a second image, which is generated based on the first volume data 315 or the detected blood vessel region, on a screen and set a cut line for the second image displayed on the screen, based on a user input. The ultrasound image display apparatus 100 may display a 3D image of the blood vessel on a screen and receive a command, which sets a cut line for the 3D image of the blood vessel displayed on the screen, from a user to set the cut line.

In FIGS. 3A (b) and (c), a case where a line segment AB (a line segment connecting a point A and a point B) parallel to a lengthwise direction of a blood vessel is set as a cut line will be described as an example. Also, when the reference plane is set as the inner wall 312 of the blood vessel, as illustrated in FIG. 3A (b) and (c), the ultrasound image display apparatus 100 may generate the second volume data 320 by mapping the volume data, included in the blood vessel region, to a plane 322 corresponding to the outer wall 311 of the blood vessel with respect to the line segment AB.

As illustrated in FIG. 3A (b), the ultrasound image display apparatus 100 may set the line segment AB as the cut line, and then set a line segment CD, corresponding to the line segment AB, as an auxiliary line. The ultrasound image display apparatus 100 may determine a point C which is disposed on a plane vertical to a blood vessel including the point A and is farthest away from the point A among points corresponding to the inner wall 312 of the blood vessel. The ultrasound image display apparatus 100 may determine a point D which is disposed on a plane vertical to a blood vessel including the point B and is farthest away from the point B among the points corresponding to the inner wall 312 of the blood vessel. The line segment CD which connects the determined points C and D may be set as an auxiliary line. In FIG. 3A, a case where a cut line and an auxiliary line are straight lines is described as an example, but the present embodiment is not limited thereto. For example, the cut line and the auxiliary line may be curves.

That is, the image processor 120 may cut the blood vessel region 315 (which is the first region) along the cut line (for example, line segment AB) parallel to the lengthwise direction of the tubular tissue, display a reference plane 322 (in detail, a surface (for example, a surface constituting an inner side of the tubular tissue) constituting a tubular tissue on the outer wall 311 of the blood vessel) by unfolding the cut blood vessel region 315 as illustrated in FIG. 3A (c), and generate a 3D image by rendering the first image, for example, the second volume data 320.

Referring to FIG. 3A (c), the reference plane is a plane which is generated by connecting vertexes A', A", B" and B', and may correspond to the outer wall 311 of the tubular tissue. Also, the reference plane is a curved plane which is generated by connecting surfaces O', O''', P''' and P' constituting the tubular tissue, and may correspond to the inner wall 312 which is a surface constituting an inner side of the tubular tissue.

Referring to FIG. 3A (d), plaques 331 and 332 which are certain tissues which are located inside the tubular tissue are illustrated.

The image processor 320 may generate the first image displayed as illustrated in FIG. 3A (c). The user easily checks the plaques 331 and 332 and a state of the blood vessel by using the first image.

In detail, the ultrasound image display apparatus 100 may make both ends of the plane 322, corresponding to the inner wall 312 of the blood vessel included in the second volume data 320, correspond to the line segment AB which is set as a cut line for the blood vessel region.

That is, in the blood vessel region 315 detected from the first volume data 310, a curved surface ABCD corresponding to a right inner wall of the blood vessel may correspond to a plane A"B"D'C' of the second volume data 320. Also, in the blood vessel region 315 detected from the first volume data 310, a curved surface ABCD corresponding to a left inner wall of the blood vessel may correspond to a plane A'B'D'C' of the second volume data 320. In the blood vessel region 315 detected from the first volume data 310, a center point O between the point A and the point C may correspond to a line O'O"O''' of the second volume data 320. Also, in the blood vessel region 315 detected from the first volume data 310, a center point P between the point B and the point D may correspond to a line P'P"P''' of the second volume data 320.

A top of the second volume data 320 may be a plane or a curved surface according to whether a thickness of the blood vessel is constant. In FIG. 3A, a case where the top of the second volume data 320 is a curved surface due to a fine thickness difference of the blood vessel is illustrated as an example.

In operation S250, the ultrasound image display apparatus 100 according to exemplary embodiments may generate a first image 330, representing information about plaque included in the blood vessel, by using the second volume data 320. The ultrasound image display apparatus 100 may render the second volume data 320 to generate the first image 330 representing the information about the plaque included in the blood vessel. Examples of the first image 330 may include a 2D image, a 3D image, and a stereoscopic image.

The ultrasound image display apparatus 100 may detect a plaque region, corresponding to the plaque, from the second volume data 320. For example, the ultrasound image display apparatus 100 may analyze brightness of pixels included in the second volume data 320 in a direction from a top O'O"O'''P'''P"P' to a bottom A'C'A"B"D'B' of the second volume data 320. The ultrasound image display apparatus 100 may detect a peak of the plaque region, based on a change in the brightness of the pixels. The ultrasound image display apparatus 100 may analyze a certain region near the detected peak as corresponding to one plaque. For example, a watershed algorithm and a method similar to a watershed algorithm may be used for detecting the plaque region.

Moreover, the ultrasound image display apparatus 100 may detect a boundary of the plaque region by using, for example, an edge mask such as a Sobel mask, a Prewitt mask, a Robert mask, a Laplacian of Gaussian mask, or a Canny mask or by using intensity or gradient. The ultrasound image display apparatus 100 may determine the plaque region, based on the detected boundary of the plaque region.

As illustrated in FIG. 3A (d), the ultrasound image display apparatus 100 may render the second volume data 320 of FIG. 3A (c) to generate the first image 330 which represents information about the plaques 331 and 332 included in the blood vessel.

In detail, in FIG. 3A (d), in the first image 330 where the blood vessel is unfolded, an image where a surface of the blood vessel is three-dimensionally expressed is illustrated.

The ultrasound image display apparatus 100 according to exemplary embodiments may provide the first image 330 which is generated by rearranging plaque, which is located on an inner wall of a cylindrical blood vessel, on a plane and thus enables the user to quickly and accurately recognize a shape, a size, a height, and a position distribution of the plaque which is located on the inner wall of the blood vessel. In detail, the ultrasound image display apparatus 100 may mark the plaques 331 and 332 on the first image 330 by applying at least one selected from different colors, shapes, and marks according to sizes, heights, and positions of the plaques 331 and 332 so as to easily check a shape, a size, a height, and a position of the plaque which exists in the first image 330.

In FIG. 3A, a tissue (for example, plaque) which protrudes inward into a tubular tissue is illustrated. Also, a tissue which protrudes in an outer direction of the tubular tissue or a tissue which passes through the tubular tissue may exist.

Figure 3B:
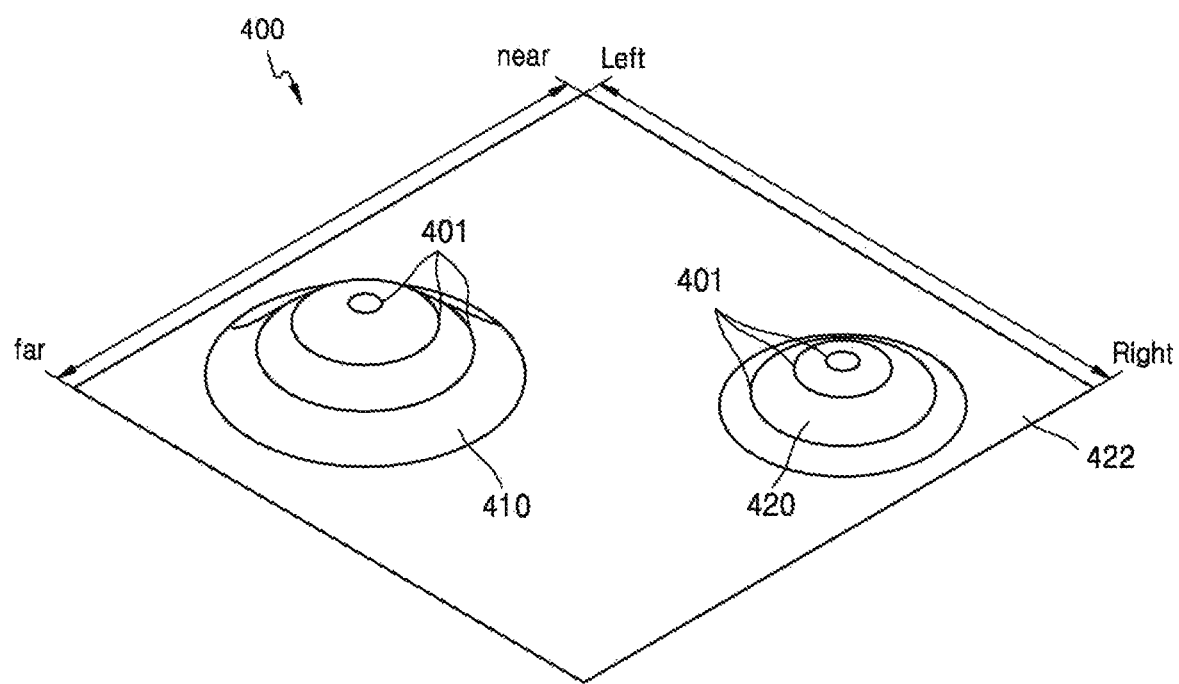
FIG. 3B illustrates an example of a screen that displays a plaque image where a contour is marked, according to exemplary embodiments.

FIG. 3B illustrates an example of a screen that displays a plaque image where a contour is marked, according to exemplary embodiments. A first image 400 illustrated in FIG. 3B may correspond to the first ultrasound image 330 illustrated in FIG. 3A (d). The image processor 120 may detect a plaque region corresponding to plaque, based on ultrasound data and generate a plaque image representing the plaque region. Also, the image processor 120 may generate a first image including the plaque image. That is, the image processor 120 may generate the plaque image as the first image.

Moreover, the image processor 120 may generate a plaque image where a contour is marked, based on a height of the plaque region.

In detail, as illustrated in FIG. 3B, the ultrasound image display apparatus 100 may generate the first image 400 including a plaque image which represents a plurality of plaque regions 410 and 420. The ultrasound image display apparatus 100 may render volume data corresponding to the detected plaque regions 410 and 420 to generate the first image 400.

The ultrasound image display apparatus 100 may generate a plaque image where a contour 401 is marked, based on the height of the plaque region. A user easily checks a shape and a size of each of the plaque regions 410 and 420 with reference to the contour 401.

Moreover, the image processor 120 may generate the first image 400 which is displayed by mapping different colors according to the contour 401. That is, by differentially displaying the first image 400 in different colors according to a height of the plaque, the image processor 120 may generate the first image 400 so as to intuitively check the height of the plaque and a degree of occurrence of the plaque.

Moreover, the image processor 120 may map at least one color to a plaque region to generate a plaque image, based on at least one selected from a ratio of a height of the plaque region and a diameter of a blood vessel, an elasticity value of the plaque region, and a brightness value of an image in the plaque region.

Figure 4A:
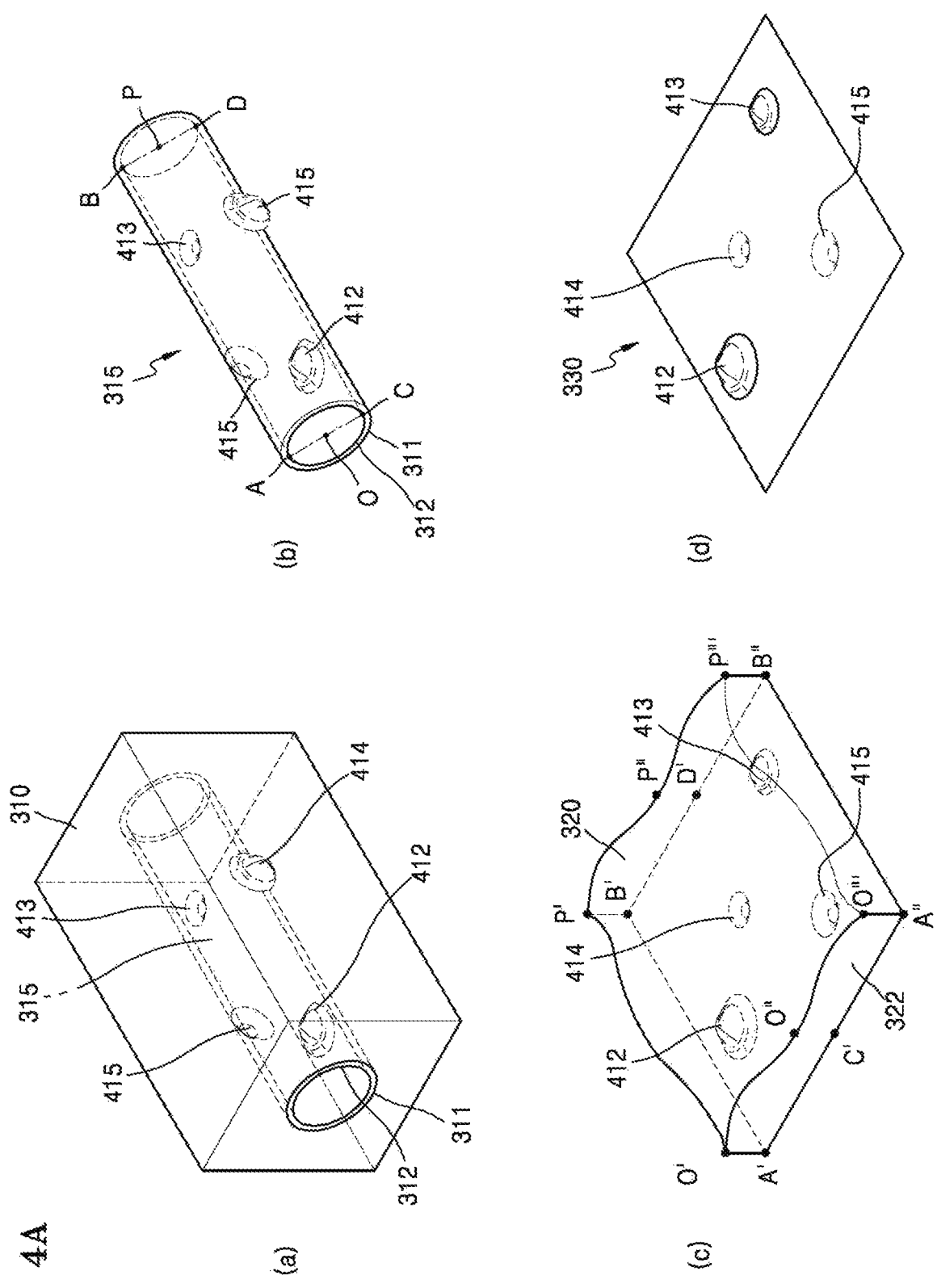
FIG. 4A is a conceptual diagram for describing a method of generating a first image according to exemplary embodiments.

FIG. 4A is a conceptual diagram for describing a method of generating a first image according to exemplary embodiments. In FIG. 4A, the same elements as those of FIG. 3A are referred to by like reference numerals. Thus, in describing FIG. 4A, the same descriptions provided with regard to FIG. 3A are not repeated.

In FIG. 3A, a tissue (for example, plaque) which protrudes inward into a tubular tissue is illustrated as an example.

In FIG. 4A, in addition to that the plaque protrudes inward into the tubular tissue as in FIG. 3A, a case where a plurality of plaques 414 and 415 protrude outward from a tubular tissue is illustrated as an example.

Figure 4B:
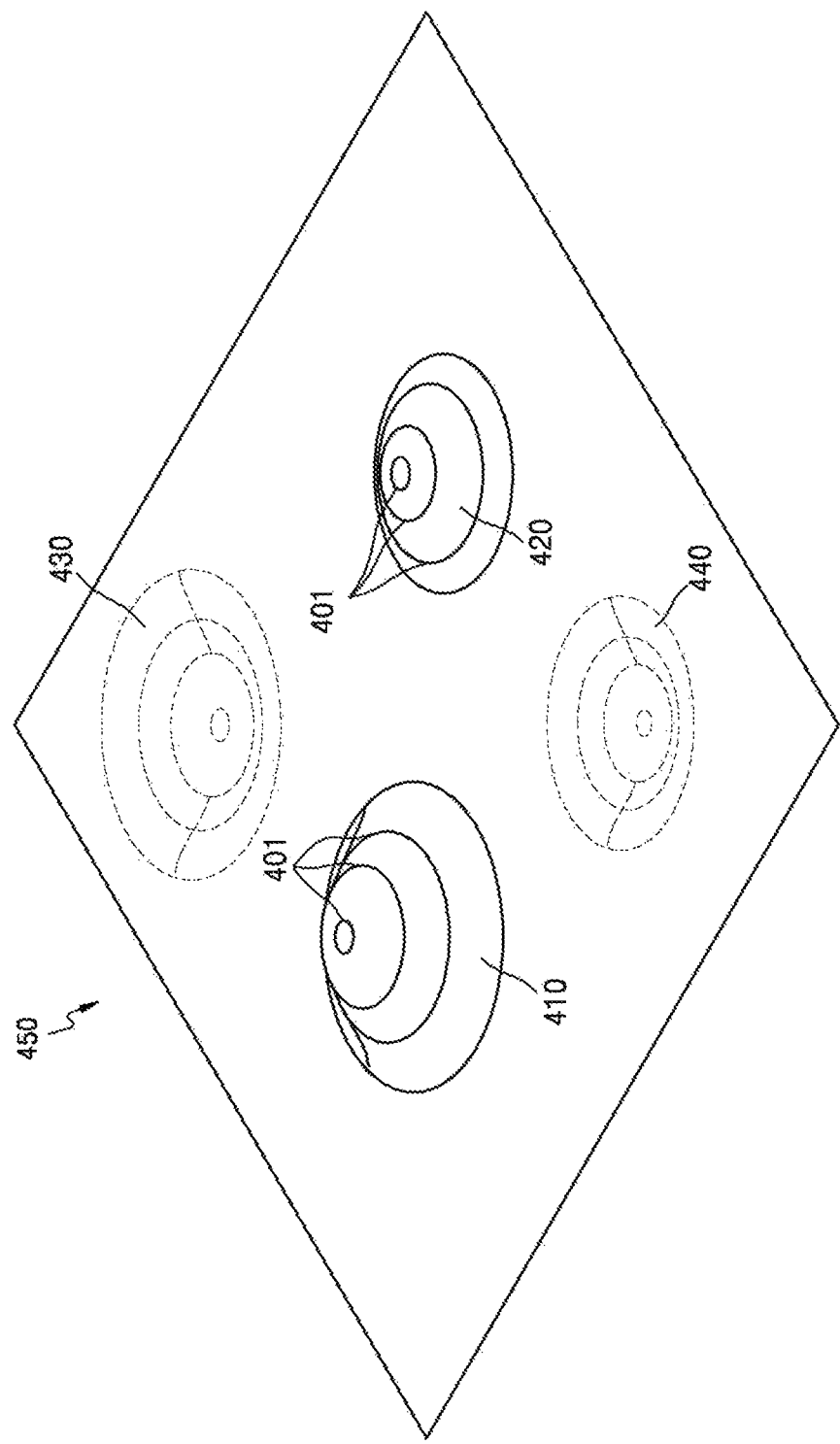
FIG. 4B illustrates an example of a screen that displays a plaque image where a contour is marked, according to exemplary embodiments.

Referring to FIG. 4B (c), a plurality of plaques 412 and 413 which protrude inward into a blood vessel and a plurality of plaques 414 and 415 which protrude outward from the blood vessel are shown in second volume data 320.

Referring to FIG. 4B (d), the plaques 412 and 413 which protrude inward into the blood vessel and the plaques 414 and 415 which protrude outward from the blood vessel are shown in a first image 330 where plaque is more clearly marked.

FIG. 4B illustrates an example of a screen that displays a plaque image where a contour is marked, according to exemplary embodiments. A first image 450 illustrated in FIG. 4B may correspond to the ultrasound image 330 illustrated in FIG. 3B (d).

Similarly to the first image 400 of FIG. 3B, in the first image 450 of FIG. 4B, a plaque image where a contour 401 is marked may be generated based on a height of a plaque region. A user easily checks a shape and a size of each of a plurality of regions 410, 420, 430 and 440 with reference to the contour 401.

The image processor 120 may generate a plaque image so that plaque which protrudes inward into a tubular tissue with reference to a reference plane and plaque which protrudes outward from the tubular tissue with reference to the reference plane are differentially marked.

Figure 5A:
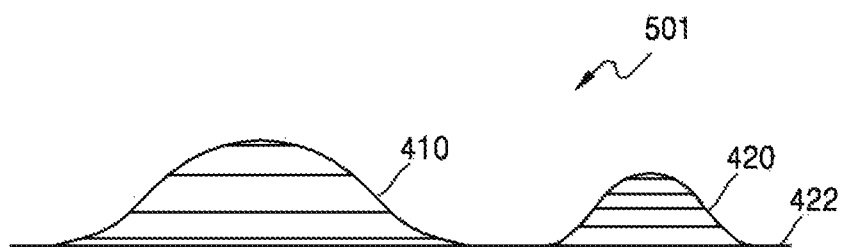
FIGS. 5A and 5B illustrate examples of a screen that displays an image obtained by rotating a first image based on a user input, according to exemplary embodiments.
Figure 5B:
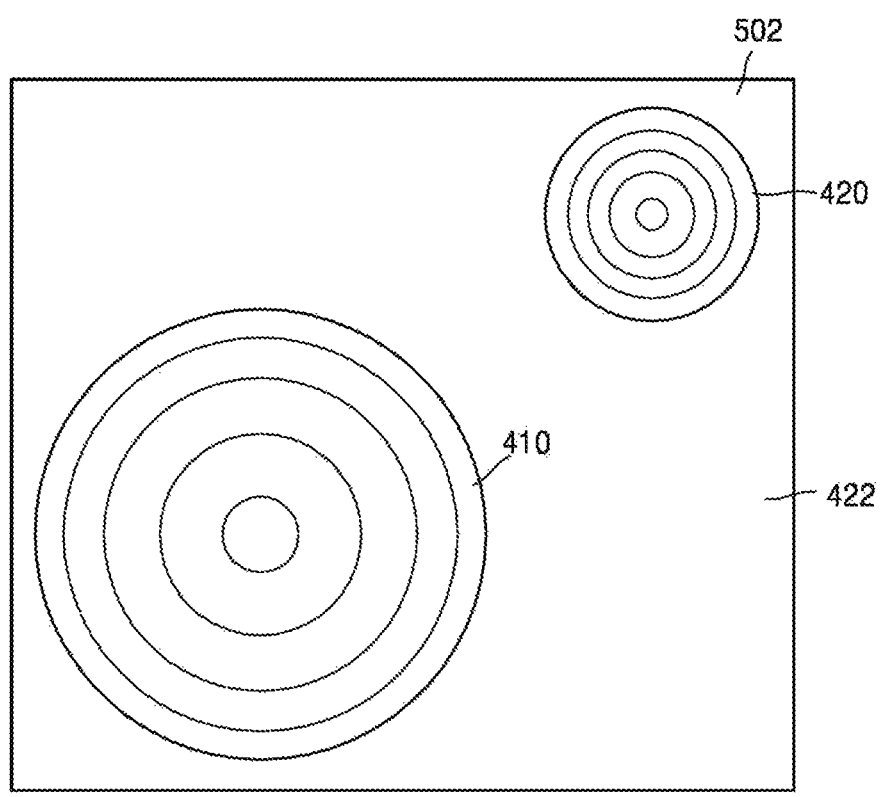

In detail, referring to FIG. 4B, each of the plaque regions 410 and 420 which are formed to protrude inward into a blood vessel may be illustrated as a solid line, and each of the plaque regions 430 and 440 which are formed to protrude outward from the blood vessel may be illustrated as a dot line. Also, by using different colors, different textures, different shapes, and different signs, the image processor 120 may generate the first image 450 so that the plaque regions 410 and 420 which are formed to protrude inward into the blood vessel and each of the plaque regions 430 and 440 which are formed to protrude outward from the blood vessel are easily distinguished. Also, as illustrated in FIGS. 5A and 5B, the ultrasound image display apparatus 100 may generate an image seen at different angles, based on a user input. That is, the ultrasound image display apparatus 100 may generate an image which is obtained by rotating a first image, based on the user input.

By rotating the first image 400 of FIG. 3B, as illustrated in FIG. 5A, the ultrasound image display apparatus 100 may generate an image which is rotated to look at plaque in a direction parallel to a plane 422 corresponding to an inner wall of a blood vessel. According to FIG. 5A, a user easily checks heights of the plaque regions 410 and 420.

In detail, the user interface 140 may receive a user input which requests a movement of the first image 400 in addition to at least one selected from a rotation and a translation of the first image 400. Then, the image processor 120 may generate and output a first image which is translated according to the user input.

Moreover, by rotating the first image 400 of FIG. 3B, as illustrated in FIG. 5B, the ultrasound image display apparatus 100 may generate an image which is rotated to look at plaque in a direction vertical to the plane 422 corresponding to the inner wall of the blood vessel. According to FIG. 5B, the user easily checks shapes of the plaque regions 410 and 420.

Figure 6A:
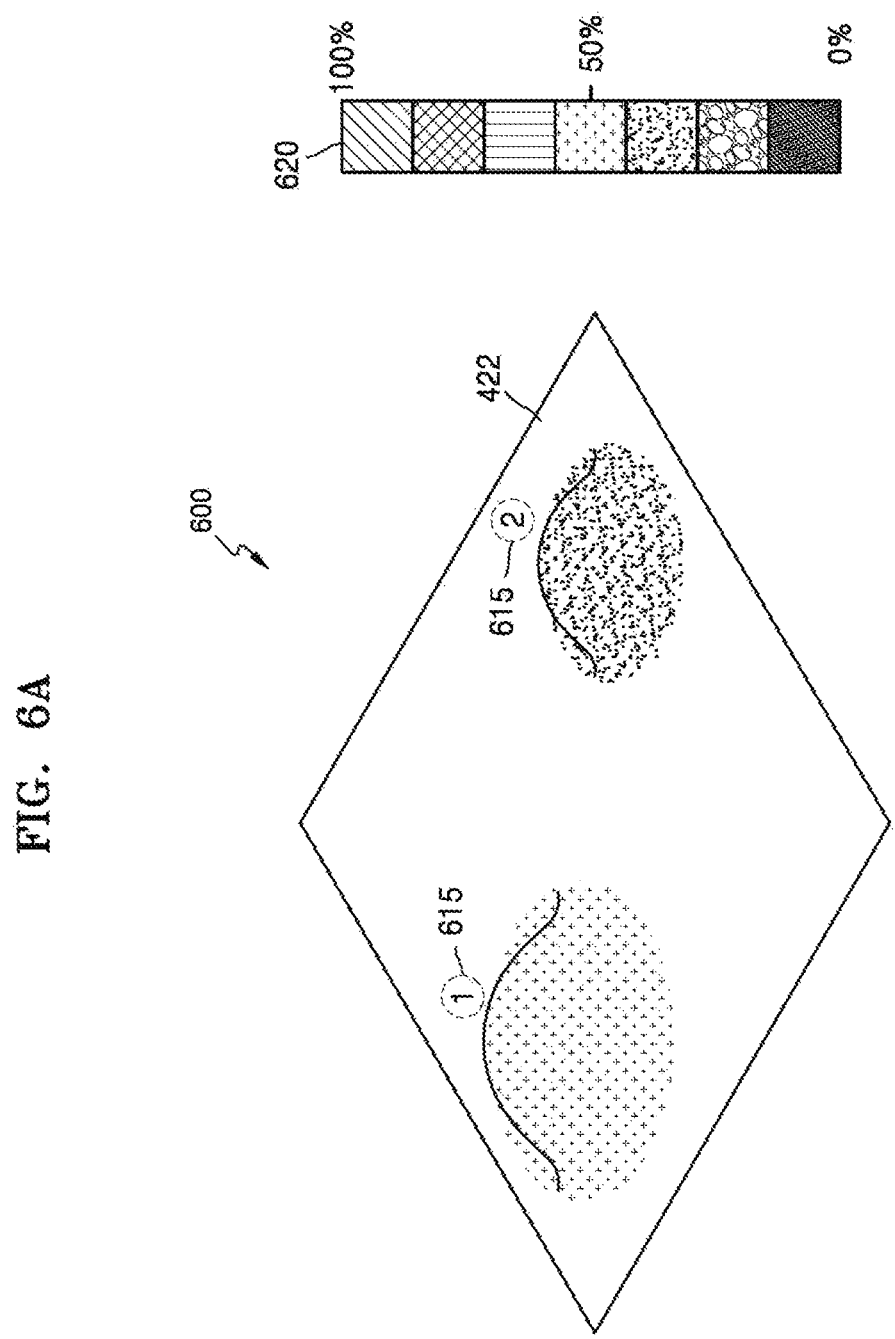
FIG. 6A illustrates an example of a screen that displays a plaque image to which at least one color is mapped, according to exemplary embodiments.

FIG. 6A illustrates an example of a screen that displays a plaque image to which at least one color is mapped, according to exemplary embodiments. A plaque image 600 illustrated in FIG. 6A is an image corresponding to the first image or the plaque image illustrated in FIG. 3A (d) or FIG. 3B.

As illustrated in FIG. 6A, the ultrasound image display apparatus 100 may generate the plaque image 600 to which at least one color is mapped, based on the heights of the plaque regions 410 and 420. A user easily checks shapes and sizes of the plaque regions 410 and 420 with reference to the mapped color. A screen including the plaque image 600 generated by the ultrasound image display apparatus 100 may include a map 620 including information about a plaque region. In detail, the map 620 may include a color map 620 where a height of a plaque is mapped to a plurality of colors. Here, the color map 620 is a map representing a color which is changed according to a ratio of a height of a plaque region to a diameter of a blood vessel. As illustrated, the plaque region may be displayed in a plurality of colors according to the above-described ratio of a height to a diameter.

As illustrated in FIG. 6A, a plaque region may be marked on the plaque image 600 by using one color corresponding to a height of a peak point of the plaque region. As another example, the plaque region may be marked on the plaque image 600 by using a color corresponding to a height of each point included in the plaque region, and thus, one plaque region is marked in a plurality of colors.

Moreover, the ultrasound image display apparatus 100 may detect the plurality of plaque regions 410 and 420 and generate the plaque image 600 which includes a plurality of identifiers 615 respectively corresponding to the plurality of plaque regions 410 and 420. For example, the plurality of identifiers 615 may include a number allocated to each plaque region. For example, the ultrasound image display apparatus 100 may allocate a priority, based on at least one selected from a height, a length, an area, and a volume of each of the detected plaque regions 410 and 420 and mark a number, corresponding to the allocated priority, on the plaque image 600.

In operation S260, the ultrasound image display apparatus 100 may display the first image which is generated in operation S250. In detail, the first image may be displayed on a screen by the display 130.

As illustrated in FIG. 3B, the ultrasound image display apparatus 100 may further display direction information in order for the user to easily check which part of a blood vessel the plane 422 corresponding to an inner wall of the blood vessel corresponds to. For example, direction information of the plane 422 may be marked as far, near, left, and right. The user may know that a far—near direction is a length of the blood vessel, based on the direction information illustrated in FIG. 3B. Also, the user may know that the far—near direction is a direction parallel to a direction in which blood flows, and may know that a left—right direction is a direction vertical to a direction in which the blood flows.

Moreover, the ultrasound image display apparatus 100 may determine and display the seriousness of stenosis of a blood vessel, based on at least one selected from a height, a length, an area, and a volume of the plaque region. The ultrasound image display apparatus 100 may determine a degree of risk of a disease (for example, arteriosclerosis, etc.) caused by the stenosis of the blood vessel, based on a guideline and display the degree of risk of the disease by using a color, a sign, a number, or a letter, etc.

Figure 6B:
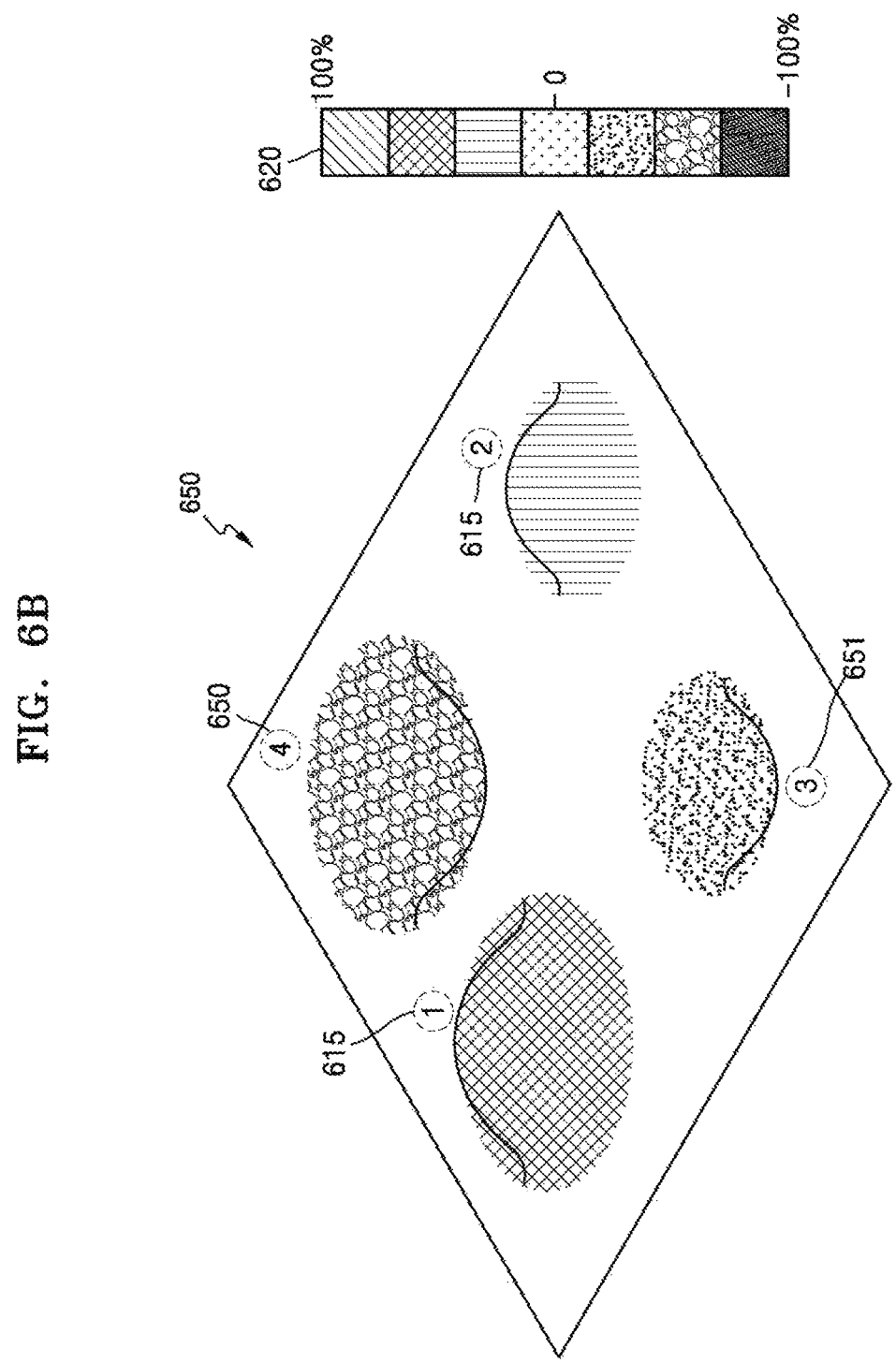
FIG. 6B illustrates an example of a screen that displays a plaque image to which at least one color is mapped, according to exemplary embodiments.

FIG. 6B illustrates an example of a screen that displays a plaque image to which at least one color is mapped, according to exemplary embodiments. A plaque image 650 illustrated in FIG. 6B is an image corresponding to the first image or the plaque image illustrated in FIG. 4A (d) or FIG. 4B.

The plaque image 650 of FIG. 6B includes a plaque region (a plaque region referred to by 615) which protrudes inward into a blood vessel and a plaque region (a plaque region referred to by 651) which protrudes outward from the blood vessel. Also, a screen including the plaque region 650 may include a map 620 representing information about the plaque region 650. The map 620 of FIG. 6B is the same as the map 620 of FIG. 6A, and thus, its detailed description is not provided.

Moreover, in a plaque region, a plaque region which is formed to protrude inward into a blood vessel and a plaque region which is formed to protrude outward from the blood vessel may be marked as marks having different signs. In detail, a (+) marker may be marked in the plaque region which is formed to protrude inward into the blood vessel, and a (−) marker may be marked in the plaque region which is formed to protrude outward from the blood vessel.

Moreover, in the map 620, −100% indicates a ratio of a height to a diameter in the plaque region which is formed to protrude outward from the blood vessel, and +100% indicates a ratio of a height to a diameter in the plaque region which is formed to protrude inward into the blood vessel.

Figure 7A:
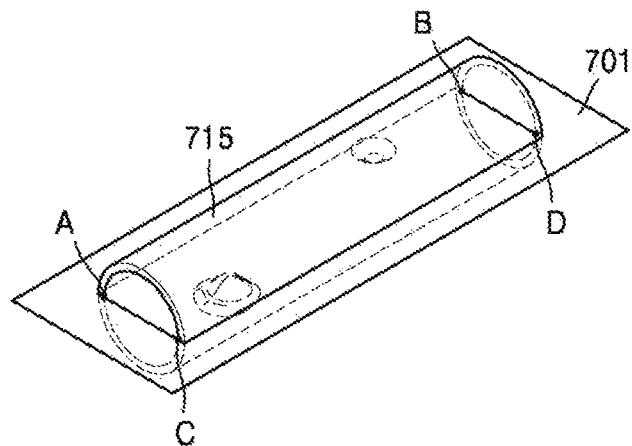
FIGS. 7A through 7C are conceptual diagrams for describing a third image that is generated with respect to a plane corresponding to a cross-sectional plane of a blood vessel, according to exemplary embodiments.

As illustrated in FIG. 7A, the ultrasound image display apparatus 100 may set a cross-sectional surface 701 of a blood vessel region 715 detected from first volume data, and generate third volume data, based on the cross-sectional surface 701. The ultrasound image display apparatus 100 may automatically or manually set the cross-sectional surface 701.

Figure 7B:
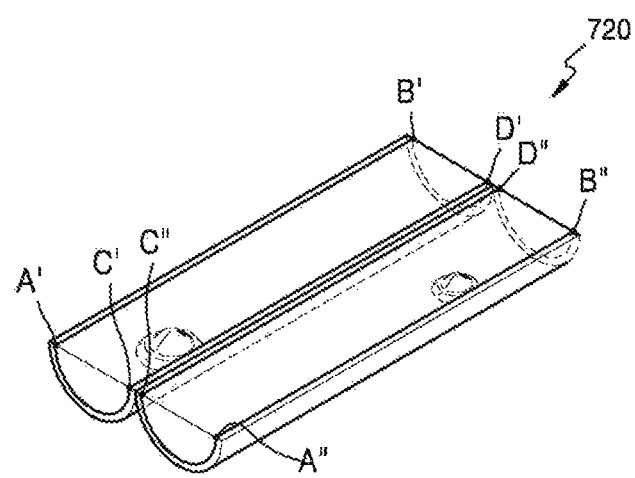
Figure 7C:
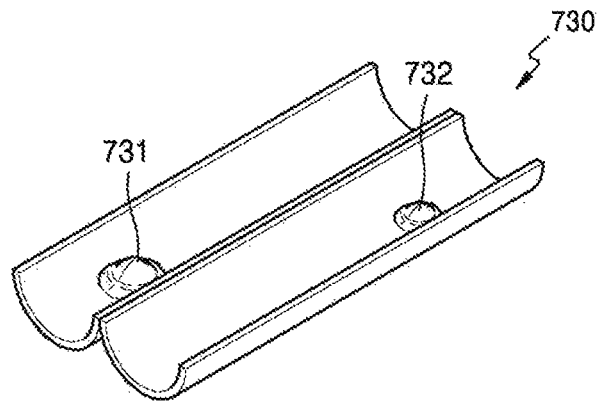

In FIGS. 7B and 7C, a case where a plane ACBD is set as a cross-sectional surface will be described as an example. As illustrated in FIGS. 7B and 7C, the ultrasound image display apparatus 100 may generate third volume data 720 by mapping volume data, included in the blood vessel region 715, to a plane A'C'C"A"B"D"D'B' corresponding to the plane ACBD.

As illustrated in FIG. 3A (c), the ultrasound image display apparatus 100 may detect a plurality of plaque regions 731 and 732 corresponding to plaque from the third volume data 720 and generate a 3D image 730 representing the plaque regions 731 and 732.

As described above, the ultrasound image display apparatus 100 according to exemplary embodiments may acquire a 3D image of the inside of a blood vessel to extract an accurate plaque region, thereby displaying a severity of calcification or petrolization of the blood vessel. Accordingly, a speed and an accuracy of a disease diagnosis increase.

Figure 8A:
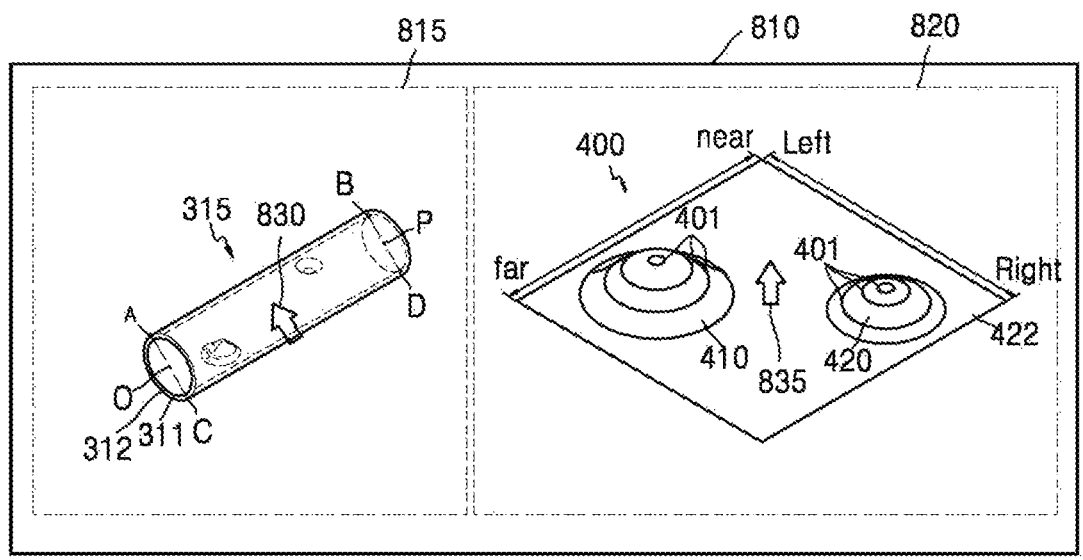
FIGS. 8A and 8B illustrate examples of a screen including a first image displayed, according to exemplary embodiments.
Figure 8B:
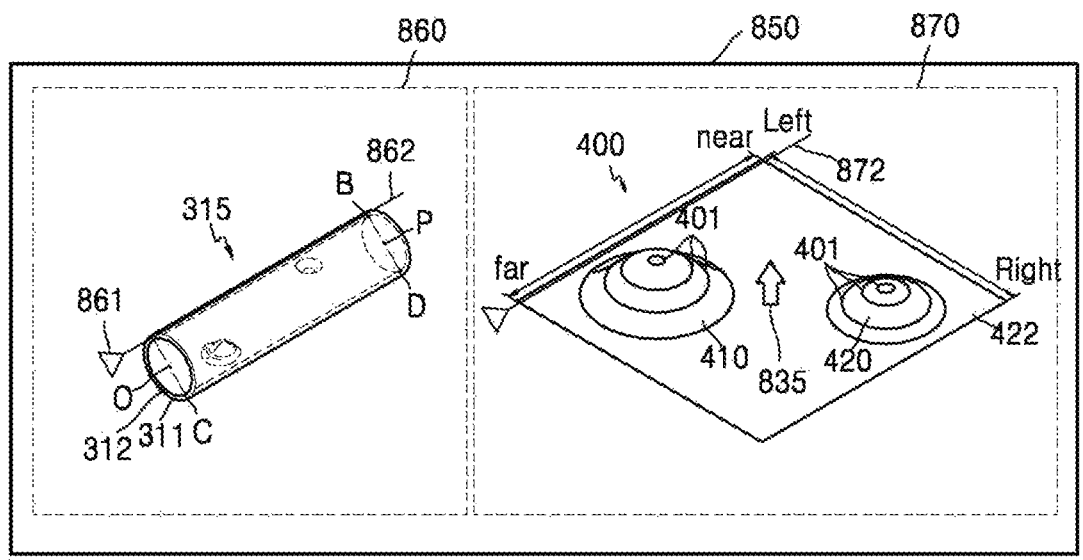

FIGS. 8A and 8B illustrate examples of a screen including a first image displayed, according to exemplary embodiments. In detail, FIGS. 8A and 8B illustrate examples of screens displayed by the display 130.

Referring to FIG. 8A, a screen 810 may include a first image 820. The first image 820 may include at least one selected from the image of FIG. 3A (c) and the image 400 of FIG. 3B. In FIG. 8A, a case where the first image 820 corresponds to the image 400 of FIG. 3B is illustrated as an example.

Moreover, a user may move the first image 820 by using a movement cursor 835. Here, movement may include at least one selected from a translation and a rotation of the first image 820.

Moreover, the image processor 120 may generate a second image 815 representing a part of an object including a tubular tissue by using ultrasound data. In detail, the second image 815 may be a 3D ultrasound image which is generated based on first volume data acquired based on the ultrasound data and represents the tubular tissue. In detail, the second image 815 may include at least one selected from the image of FIG. 3A (a) and the image of FIG. 3A (b). That is, the second image 815 may be a 3D ultrasound image representing an object which includes the tubular tissue. Also, the second image 815 may be a 3D ultrasound image representing only the tubular tissue extracted from the object.

Moreover, a screen 810 may include the first image 820 and the second image 815.

Moreover, when the first image 820 is moved and displayed according to a user input based on the movement cursor 835, the second image 815 may also be moved and displayed to correspond to the first image 820.

Moreover, the user may move the second image 815 by using the movement cursor 835. Also, when the second image 815 is moved and displayed according to a user input based on the movement cursor 835, the first image 820 may also be moved and displayed to correspond to the second image 815.

Referring to FIG. 8B, a first image 870 included in a screen 850 may include a plurality of markers 871 and 872 for displaying a cut line. In describing a screen 850 illustrated in FIG. 8B, the same descriptions provided with regard to the screen 810 of FIG. 8A are not repeated.

Moreover, in describing a second image 860, a plurality of markers 861 and 862 may be included in a part corresponding to the cut line of the first image 870. That is, each of the marker 861 and a marker 871 is a marker for marking a point where a cut line exists in a circumference of a blood vessel. Also, each of the marker 862 and a marker 872 is a marker indicating a cut line.

The user easily checks a position relationship between an unfolded tubular tissue and a folded tubular tissue while looking at markers which are marked at positions, corresponding to each other, of the first image 870 and the second image 860.

Figure 9A:
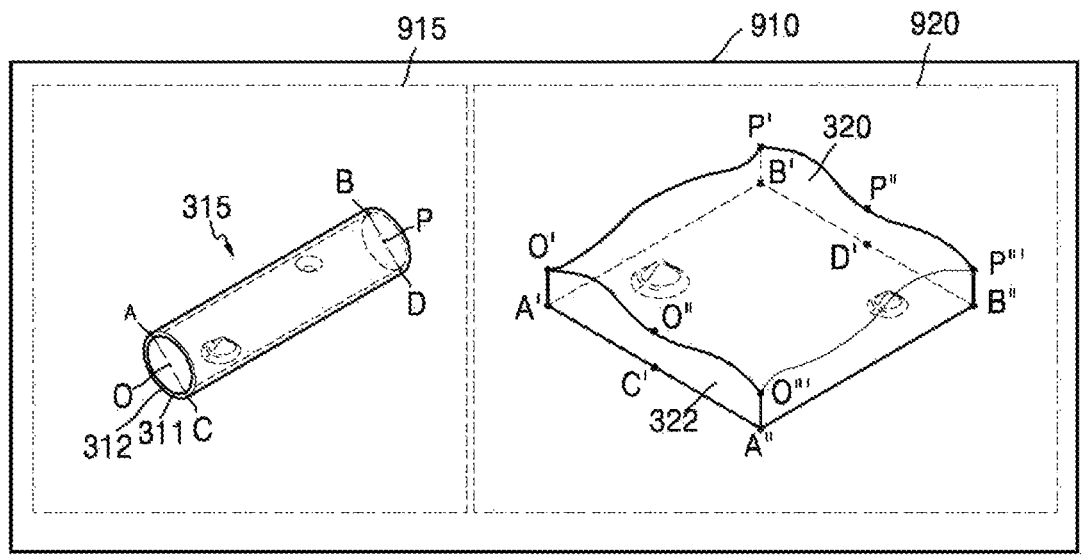
FIGS. 9A and 9B illustrate examples of a screen including a first image displayed, according to exemplary embodiments.
Figure 9B:
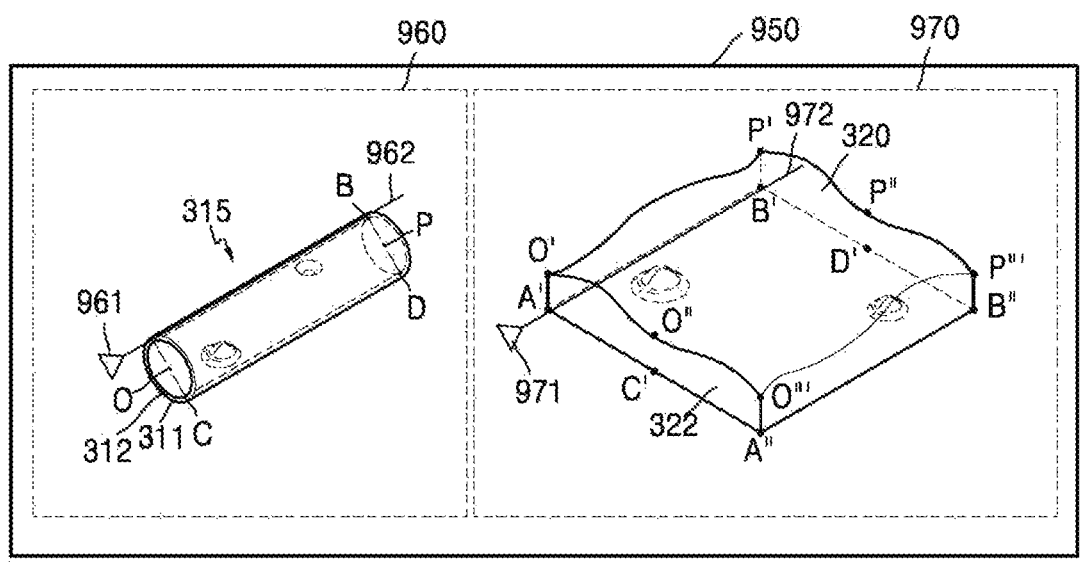

FIGS. 9A and 9B illustrate, examples of a screen including a first image displayed, according to exemplary embodiments. In detail, FIGS. 9A and 9B illustrate examples of screens displayed by the display 130.

Referring to FIG. 9A, a screen 910 may include a first image 920. In FIG. 9A, a case where the first image 920 corresponds to the image of FIG. 3A (c) is illustrated as an example. Also, the screen 910 may further include a second image 915. In describing a screen 910 illustrated in FIG. 9A, the same descriptions provided with regard to the screen 810 of FIG. 8A are not repeated.

Referring to FIG. 9B, a screen 950 may include a first image 970. In FIG. 9B, a case where the first image 970 corresponds to the image of FIG. 3A (c) is illustrated as an example. Also, the screen 950 may further include a second image 960.

Moreover, a plurality of markers 971 and 972 for marking a cut line may be included in the first image 970. Also, in the second image 960, a plurality of markers 961 and 962 may be included in a part corresponding to the cut line of the first image 970.

In describing the screen 950 illustrated in FIG. 9B, the same descriptions provided with regard to the screen 850 of FIG. 8B are not repeated.

Moreover, a screen (not shown) including a first image (for example, 810 or 910) may additionally display information about a size, a height, a volume, a brightness, or a severity of at least one (hereinafter referred to as a sensing tissue) (for example, plaque in a blood vessel) selected from a certain part and a certain tissue which are sensed in a tubular tissue. For example, the screen (not shown) may display information in which at least one selected from a size, a height, and a volume of the sensing tissue is numerically marked.

As described above, the ultrasound image display apparatus and method according to exemplary embodiments generate and display an ultrasound image which three-dimensionally represents an unfolded tubular tissue on a reference plane, thereby enabling a user to easily diagnose the inside and the outside of the tubular tissue. Accordingly, an accuracy of a disease diagnosis increases.

FIG. 10 is a block diagram of an ultrasound system 1000 to which an ultrasound image display apparatus is applied, according to exemplary embodiments.

The ultrasound image display method according to exemplary embodiments may be performed by the ultrasound system 1000 of FIG. 10, and the ultrasound image display apparatus according to exemplary embodiments may be included in the ultrasound system 1000 of FIG. 10.

The ultrasound image display apparatus 100 of FIG. 1 may perform all or some of functions performed by the ultrasound system 1000 of FIG. 10. The probe 110 and the image processor 120 of FIG. 1 may correspond to a probe 1020, an ultrasound transceiver 1100, and an image processor 1200 of FIG. 10. The display 130 of FIG. 1 may correspond to a display 1700 of FIG. 10. The user interface 140 of FIG. 1 may correspond to an input device 1500 of FIG. 10.

FIG. 10 is a block diagram showing a configuration of an ultrasound diagnosis apparatus 1000 according to an embodiment. Referring to FIG. 10, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 included in a data processor 1210 extracts B mode components from ultrasound data and processes the B mode components. An image generator 1220 may generate an ultrasound image indicating signal intensities as brightness based on the extracted B mode components 1212.

Similarly, a Doppler processor 1214 included in the data processor 1210 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 10.

All or some of the probe 20, the ultrasound transceiver 1100, the image processor 1200, the communication module 1300, the display 1400, the memory 1500, the input device 1600, and the controller 1700 may be implemented as software modules. Furthermore, at least one selected from the ultrasound transceiver 1100, the image processor 1200, and the communication module 1300 may be included in the controller 1600. However, exemplary embodiments are not limited thereto.

The exemplary embodiments may be implemented in the form of a storage medium that includes computer executable instructions, such as program modules, being executed by a computer. Computer-readable media may be any available media that may be accessed by the computer and includes both volatile and nonvolatile media, removable and non-removable media. In addition, the computer-readable media may include computer storage media and communication media. Computer storage media includes both volatile and non-volatile, removable and non-removable media implemented as any method or technology for storage of information such as computer readable instructions, data structures, program modules, or other data. The medium of communication is typically computer-readable instructions, and other data in a modulated data signal such as data structures, or program modules, or other transport mechanism and includes any information delivery media.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. An ultrasound image display apparatus comprising:
   an image processor that generates a first image three-dimensionally representing a surface constituting a tubular tissue on a reference plane, based on ultrasound data corresponding to an object including the tubular tissue; and
   a display that displays the first image,
   wherein the image processor detects a plurality of plaque regions corresponding to a plurality of plaques in the tubular tissue, based on the ultrasound data, and generates a plaque image, reflecting a height of each of the plaque regions, in which at least one plaque among the plaques formed to protrude inward into the tubular tissue and at least one plaque among the plaques formed to protrude outward from the tubular tissue are distinguished from each other,
   wherein the image processor generates a map representing information regarding a direction in which each of the plaques protrudes from the tubular tissue and the height of each of the plaque regions, wherein the height of each of the plaque regions is mapped to at least one color, based on a ratio of the height of each of the plaque regions to a diameter of the tubular tissue.

2. The ultrasound image display apparatus of claim 1, wherein the first image is a three-dimensional (3D) image that represents an unfolded surface constituting the tubular tissue.

3. The ultrasound image display apparatus of claim 1, wherein the image processor senses at least one selected from a certain part and a certain tissue which are located on the surface constituting the tubular tissue, based on the ultrasound data and marks at least one selected from the sensed certain part and the sensed certain tissue on the surface constituting the tubular tissue to generate the first image.

4. The ultrasound image display apparatus of claim 1, wherein the image processor acquires first region data that includes at least one selected from at least two two-dimensional (2D) ultrasound images enabling a three-dimensional shape of the tubular tissue to be acquired and three-dimensional (3D) data three-dimensionally expressing the tubular tissue, based on the ultrasound data and generates the first image, based on the first region data.

5. The ultrasound image display apparatus of claim 4, wherein the image processor detects a first region corresponding to the tubular tissue from first volume data which is acquired based on the ultrasound data, maps the first volume data corresponding to the first region to the reference plane to generate second volume data, and generates the first image, based on the second volume data.

6. The ultrasound image display apparatus of claim 4, wherein the image processor acquires a plurality of two-dimensional (2D) ultrasound images corresponding to a plurality of continuous slices, based on the ultrasound data, acquires a three-dimensional shape of the tubular tissue, based on the plurality of 2D ultrasound images, and generates the first image, based on the three-dimensional shape of the tubular tissue.

7. The ultrasound image display apparatus of claim 1, wherein,
   the tubular tissue comprises a blood vessel,
   the image processor detects a first region corresponding to the blood vessel from first volume data which is acquired based on the ultrasound data,
   the first region comprises a blood vessel region, and
   the image processor generates the first image representing information about plaque included in the blood vessel.

8. The ultrasound image display apparatus of claim 7, wherein the image processor generates the first image including the plaque image.

9. The ultrasound image display apparatus of claim 8, wherein the image processor generates the plaque image in which a contour is marked, based on the height of each of the plaque regions.

10. The ultrasound image display apparatus of claim 8, wherein the image processor generates the plaque image to which the at least one color determined based on the height of each of the plaque regions is mapped.

11. The ultrasound image display apparatus of claim 8, wherein the image processor maps the at least one color to each of the plaque regions to generate the plaque image, further based on at least one selected from an elasticity value of each of the plaque regions, and a brightness value of the plaque image corresponding to each of the plaque regions.

12. The ultrasound image display apparatus of claim 7, wherein,
   the image processor generates the first image including the plaque image, and
   the plaque image comprises a plurality of identifiers respectively corresponding to the plurality of plaque regions.

13. The ultrasound image display apparatus of claim 1, wherein the image processor detects a first region corresponding to the tubular tissue from first volume data which is acquired based on the ultrasound data, sets a cut line for the first region in a lengthwise direction of the tubular tissue, and cuts the first region along the cut line to generate the first image that represents an unfolded surface constituting the tubular tissue.

14. The ultrasound image display apparatus of claim 1, wherein the display further displays a second image that is a three-dimensional (3D) ultrasound image that is generated based on first volume data which is acquired based on the ultrasound data and represents the tubular tissue.

15. The ultrasound image display apparatus of claim 14, further comprising a user interface that receives a first user input for setting a cut line, which is parallel to a lengthwise direction of the tubular tissue, in the second image, wherein the image processor sets the cut line for a first region corresponding to the tubular tissue included in the first volume data, based on the first user input and cuts the first region along the cut line to generate the first image that represents an unfolded surface constituting the tubular tissue.

16. The ultrasound image display apparatus of claim 1, further comprising a user interface that receives a second user input for rotating the first image, wherein the image processor performs control to display a rotated image which is obtained by rotating the first image, based on the second user input.

17. The ultrasound image display apparatus of claim 1, further comprising a probe that transmits an ultrasound signal to the object and receives an echo signal reflected from the object, wherein the image processor receives the ultrasound data including the echo signal.

18. An ultrasound image display method comprising:

generating a first image three-dimensionally representing a surface constituting a tubular tissue on a reference plane, based on ultrasound data corresponding to an object including the tubular tissue; and displaying the first image, wherein the generating the first image comprises:

detecting a plurality of plaque regions corresponding to a plurality of plaques in the tubular tissue, based on the ultrasound data; and generating a plaque image, reflecting a height of each of the plaque regions, in which at least one plaque among the plaques formed to protrude inward into the tubular tissue and at least one plaque among the plaques formed to protrude outward from the tubular tissue are distinguished from each other, wherein the displaying the first image comprises:

displaying a map representing information regarding a direction in which each of the plaques protrudes from the tubular tissue and the height of each of the plaque regions, and wherein the height of each of the plaque regions is mapped to at least one color, based on a ratio of the height of each of the plaque regions to a diameter of the tubular tissue.

\* \* \* \* \*